US012758712B2

(12) United States Patent
Lopez et al.

(10) Patent No.: US 12,758,712 B2
(45) Date of Patent: Oct. 13, 2026

(54) DEVICE FOR VIABLE NEOTISSUE AND STEM CELL TRANSPLANT AND METHODS OF INJECTION

(71) Applicant: Board of Supervisors of Louisiana State University and Agricultural and Mechanical College, Baton Rouge, LA (US)

(72) Inventors: Mandi J. Lopez, Baton Rouge, LA (US); Dorin Boldor, Baton Rouge, LA (US); Thomas Coreil, Baton Rouge, LA (US); Khoivu Dinh Nguyen, Baton Rouge, LA (US); Allison Zieschang, Baton Rouge, LA (US); Stefano Anthony Dardano, Baton Rouge, LA (US); Luz De Luna Lawes, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 670 days.

(21) Appl. No.: 18/137,743

(22) Filed: Apr. 21, 2023

(65) Prior Publication Data

US 2023/0338663 A1 Oct. 26, 2023

Related U.S. Application Data

(60) Provisional application No. 63/333,427, filed on Apr. 21, 2022.

(51) Int. Cl.
*A61M 5/19* (2006.01)
*A61M 5/31* (2006.01)

(52) U.S. Cl.
CPC ............ *A61M 5/19* (2013.01); *A61M 5/3146* (2013.01); *A61M 2005/3109* (2013.01);
(Continued)

(58) Field of Classification Search
CPC ... A61M 5/3146; A61M 5/19; A61M 2202/09
See application file for complete search history.

(56) References Cited

U.S. PATENT DOCUMENTS 5,019,045 A * 5/1991 Lee ...................... A61M 5/347 604/218
10,702,629 B2 * 7/2020 Pilkington .......... A61M 5/2448
(Continued)

FOREIGN PATENT DOCUMENTS

JP 2009034190 A * 2/2009 .......... A61B 10/025

OTHER PUBLICATIONS

Wang, Y., Jin, S., Luo, D., He, D., Shi, C., Zhu, L., Liu, Y. (2021). Functional regeneration and repair of tendons using biomimetic scaffolds loaded with recombinant periostin. Nature Communications, 12(1), 1293. doi: 10.1038/s41467-021-21545-1.
(Continued)

*Primary Examiner* — Andrew H Nguyen
(74) *Attorney, Agent, or Firm* — Thomas Horstemeyer LLP.

(57) ABSTRACT

Provided are devices and methods for injecting viable transplant tissues into a subject. The device includes a fluid exchange chamber having a funneled portion connected to a pre-injection tube. The chamber includes fluid transfer holes and is disposed in an outer shell having a central bore connecting a top inlet and a bottom outlet from which the pre-injection tube exits the shell. A plunger having a central channel and a tapered bottom is disposed in the central bore such that the tapered bottom mates the funneled bottom
(Continued)

when depressed and a stylet plunger is disposed in the central channel of the plunger.

14 Claims, 23 Drawing Sheets

(52) U.S. Cl.
CPC .................. *A61M 2005/311* (2013.01); *A61M 2005/3117* (2013.01); *A61M 2202/09* (2013.01); *A61M 2250/00* (2013.01)

(56) References Cited

U.S. PATENT DOCUMENTS

| | | | | |
|---|---|---|---|---|
| 2006/0063962 | A1* | 3/2006 | Drobnik ............... | A61N 5/1027 600/7 |
| 2013/0030322 | A1* | 1/2013 | Levine ............... | A61B 10/0283 600/566 |
| 2020/0188602 | A1* | 6/2020 | Gusenoff .............. | A61M 1/815 |

OTHER PUBLICATIONS

Andarawis-Puri, N., Flatow, E. L., & Soslowsky, L. J. (2015). Tendon basic science: Development, repair, regeneration, and healing. Journal of orthopaedic research: official publication of the Orthopaedic Research Soceity, 33(6), 780-784. https://doi.org/10.1002/jor.22869.

Amer, M. H., Rose, F., Shakesheff, K. M., & White, L. J. (2018). A biomaterials approach to influence stem cell fate in injectable cell-based therapies. Stem cell research & therapy, 9(1), 39. https://doi.org/10.1186/s13287-018-0789-1.

Paredes, J. J., & Andarawis-Puri, N. (2016). Therapeutics for tendon regeneration: a multidisciplinary review of tendon research for improved healing. Annals of the New York Academy of Sciences, 1383(1), 125-138. https://doi.org/10.1111/nyas.13228.

Yang, G., Rothrauff, B. B., & Tuan, R. S. (2013). Tendon and ligament regeneration and repair: clinical relevance and developmental paradigm. Birth defects research. Part C, Embryo today : reviews, 99(3), 203-222. https://doi.org/10.1002/bdrc.21041.

Bertuglia, A., Bullone, M., Rossotto, F. et al. Epidemiology of musculoskeletal injuries in a population of harness Standardbred racehorses in training. BMC Vet Res 10, 11 (2014). https://doi.org/10.1186/1746-6148-10-11.

* cited by examiner t Test

Stro wo pass-Stro w pass

Assuming unequal variances

| | | | |
|---|---|---|---|
| Difference | 19.6000 | t Ratio | 2.636162 |
| Std Err Dif | 7.4351 | DF | 5.377892 |
| Upper CL Dif | 38.3154 | Prob > \|t\| | **0.0430*** |
| Lower CL Dif | 0.8846 | Prob > t | **0.0215*** |
| Confidence | 0.95 | Prob < t | 0.9785 |

t Test

Teno wo pass-Teno w pass

Assuming unequal variances

| | | | |
|---|---|---|---|
| Difference | -11.600 | t Ratio | -2.09494 |
| Std Err Dif | 5.537 | DF | 7.992487 |
| Upper CL Dif | 1.171 | Prob > \|t\| | 0.0695 |
| Lower CL Dif | -24.371 | Prob > t | 0.9652 |
| Confidence | 0.95 | Prob < t | **0.0348*** |

DEVICE FOR VIABLE NEOTISSUE AND STEM CELL TRANSPLANT AND METHODS OF INJECTION

CROSS-REFERENCE TO RELATED APPLICATIONS

This application claims the benefit of and priority to U.S. Provisional Application Ser. No. 63/333,427, having the title "DEVICE FOR VIABLE NEOTISSUE AND STEM CELL TRANSPLANT AND INJECTION", filed on Apr. 21, 2022, the disclosure of which is incorporated herein by reference in its entirety.

BACKGROUND

Many injuries such as broken bones or muscle and ligament tears can affect patients and inhibit their daily lives (Paredes et al., 2016). Horses, especially equine athletes, are heavily affected by these injuries because it may completely incapacitate them and prevent them from competing, practicing, or moving in general. Injuries to the suspensory ligament, deep digital flexor tendon, and superficial digital flexor tendon are extremely common and rarely fully regenerate (Bertuglia et al., 2014). These injuries must be fixed through surgery. However, there is now a way for partial tendon tears to be fixed. There are surgical clinical trials studying the injection of artificially-grown tendon tissue into tendon lesions. This can be done to areas with partially torn tendons, so that the area may be preserved from surgery where the tissue would have to be cut open to complete the surgical procedure. The new procedure of injecting neotissue only requires that the cells be injected into the affected area which will not damage surrounding tissue or pose the same operating risks the tissue like surgical alternatives.

However, current options for injecting neotissue are not effective. Current state of the art utilizes administration of viable cells and neotissue via a standard syringe mechanism. The tissues and/or cells are exposed to environmental conditions, increasing the risk of contamination and damage. The present disclosure addresses these needs and other needs.

SUMMARY

Embodiments of the present disclosure provide devices and methods for the injection of viable neotissue into a subject.

An embodiment of the present disclosure includes an injection device for delivery of viable neotissue. The device can have a fluid exchange chamber with a funneled portion where the funneled portion has a bottom connected to a pre-injection tube. The fluid exchange chamber includes fluid transfer holes extending through an outer surface of the fluid exchange chamber. The device can also have a cylindrical outer shell comprising a central bore connecting a top inlet and a bottom outlet. The fluid exchange chamber is disposed in the outer shell and the pre-injection tube exits the shell via the bottom outlet. The device can also include a plunger with a central channel and a tapered bottom. The tapered bottom mates with the inside of the funneled bottom when the plunger is depressed. The plunger receives a stylet plunger in the central channel.

An embodiment of the present disclosure also includes a method for injecting viable neotissues into a subject that includes loading a fluid medium that includes transplant tissues into a device as above. The fluid medium is loaded into the central bore of the outer shell and the plunger and stylet are inserted into the central bore, but not fully depressed. The device includes a removable cap coupled to a Luer lock needle fitting to prevent leakage from the bottom outlet when a needle is not fitted to the device.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates device, including the path of the plunger and stylet plunger. FIG. 1B is an illustration of the device including measurements in accordance with embodiments of the present disclosure. FIG. 1C is a labeled side view. FIG. 1D is a perspective view. FIG. 1E is a top view showing the plunger.

Figure 1A:
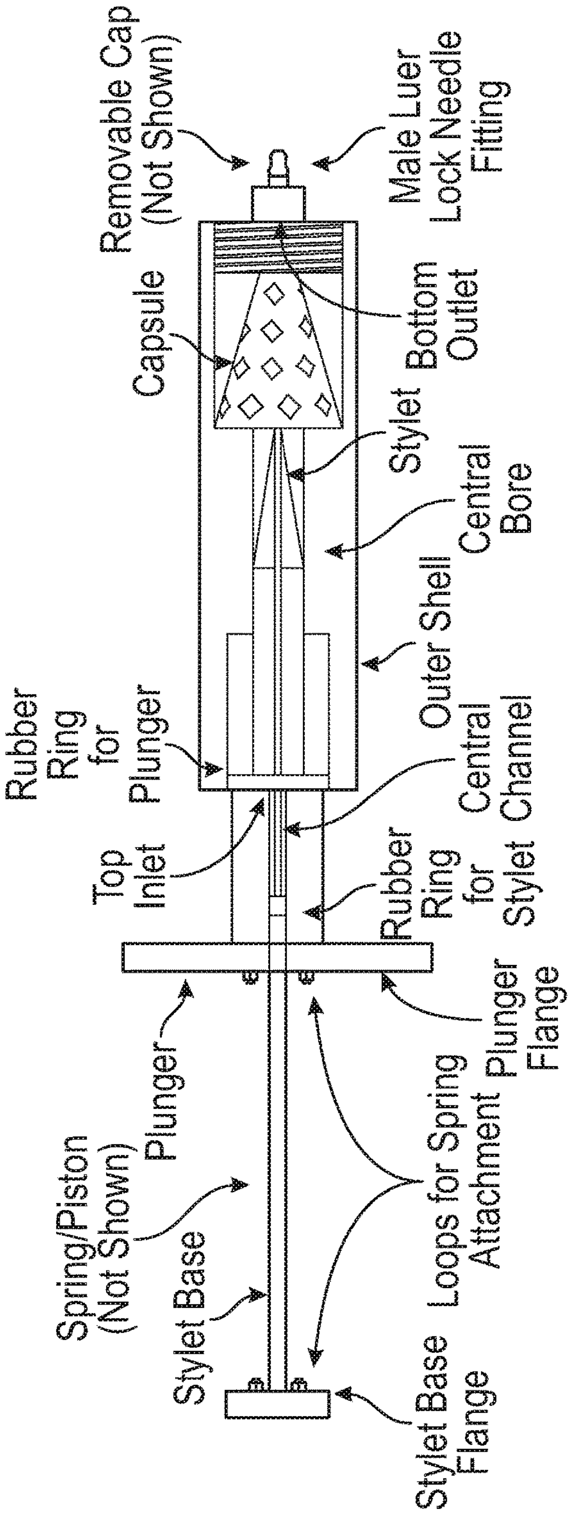
FIGS. 1A-1E are illustrations of embodiments of the device.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biomedical engineering and the like, which are within the skill of the art.

The following examples are put forth so as to provide those of ordinary skill in the art with a complete disclosure and description of how to perform the methods and use the devices disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Definitions

As used herein, neo-tissue or neotissue, refers to immature tissue engineered de novo from cells.

Engineered tissue, as used herein, refers to tissues or products that are derived from cells. The tissues can be used to repair, replace, or regenerate tissue in a recipient subject. In general, engineered tissue includes cells in matrix. The tissue component can be combined with a biomaterial such as a scaffold or growth factors. The tissue component can include whole cells or cell components, including but not limited to stem cells, progenitor cells, extracellular matrix, osteoblasts, fibroblasts, chondroblasts, and the like.

Viable cells, as used herein, refers to cells that are suitable for delivery into a subject, (e.g., alive, functional for tissue transplant).

Where the term rubber is used, it can be understood that other suitable materials that expand and compress (e.g., silicone, foam, natural rubber) can be used.

General Discussion

In accordance with the purpose(s) of the present disclosure, as embodied and broadly described herein, embodiments of the present disclosure, in some aspects, relate to devices and methods of injecting viable transplant tissues into a subject. Advantageously, the transplant tissues can be neotissue containing live cells surrounded by immature extracellular matrix or can be used to deliver matrix alone. The transplant tissue can be viable cells within a synthetic (scaffold) or natural (neotissue) matrix. The device allows transport in medium, expulsion of the medium immediately prior to injection, and subsequent injection of cells on scaffold or neotissue with a single device.

The present disclosure includes a device for delivery of engineered tissues to a subject. The device can include a fluid exchange chamber having a funneled portion, the funneled portion having a bottom connected to a pre-injection tube. The fluid exchange chamber can have fluid transfer holes through its outer surface. The device can also include a cylindrical outer shell (also referred to as a capsule), which has a central bore connecting a top inlet and a bottom outlet. The fluid exchange chamber can be disposed in the bottom of the outer shell such that the pre-injection tube exits the shell via the bottom outlet. The device also includes a plunger having a central channel and a tapered bottom. The plunger is disposed in the central bore through the top inlet. When the plunger is depressed, the tapered bottom mates with the inside of the funneled bottom. A stylet plunger is disposed in the central channel of the plunger. Advantageously, the device allows for viable tissues to be stored in a fluid medium inside the device prior to delivery and can deliver the tissues to the subject without damaging cells.

In some embodiments, the device can include a Luer lock so that a standard needle (such as an 18-gauge needle) can be coupled to the device. The device can include a removable cap that couples to the Luer lock when a needle is not coupled to the device. The device can also coupled to any gauge of needle by changing the diameter of the stylet attached to the end of the plunger to guide the neo-tissue through the attached needle.

In some embodiments, the outer shell can be a hollow cylinder, similar to a syringe. In other embodiments, the outer shell can contain interior cavities shaped to receive the fluid exchange chamber, plunger, stylet, or combinations thereof.

Embodiments of the present disclosure include a method of delivering engineered tissues using a device as above, wherein the method includes loading a fluid medium comprising transplant tissues into a device as above. The fluid medium is then loaded into the central bore of the outer shell and the plunger and stylet are inserted into the central bore to seal the fluid medium inside the device. To inject the tissues into the subject, the plunger is depressed to expel excess fluid from the tissues. The needle is fitted to the Luer lock and inserted into an injury site. The stylet plunger is depressed to direct the tissues through the pre-injection tube, through the needle, and into the injury site.

In various embodiments, the transplant tissue can include neo-tissues, engineered tissues, and the like, wherein the tissue contains viable cells. The neo-tissues, in some embodiments, can be tendon neotissue generated de novo from adult adipose-derived multipotent stromal cells. Other tissue types can be used as can be envisioned by one of ordinary skill in the art.

The devices and methods as described herein can be used for procedures including tendon repair, cartilage repair, dermal and subdermal injections such as for plastic surgery, ligament repair, and the like. The subjects receiving treatment can be human, equine, or other animals.

In various embodiments, the device can be manufactured using additive manufacturing, injection molding, or other manufacturing methods as can be envisioned by one of ordinary skill in the art.

In some embodiments, the fluid exchange chamber can be coupled to the inside of the outer shell by complementary threads. In other embodiments, the fluid exchange chamber and the outer shell can be connected by such as a snap connection. In yet other embodiments, the outer shell and fluid exchange chamber can be a singular part created by injection molding.

In some embodiments, the plunger can have a flange at the top end to aid a user in depressing the plunger and to prevent the plunger from being depressed too deeply into the central bore. The plunger can also include a flexible seal or gasket (e.g., a rubber or silicone ring) that prevents fluid from escaping the top inlet and prevents contaminants from entering.

In some embodiments, the stylet plunger can have a flange and a base. At the bottom end, the stylet plunger can have a cavity to receive a stylet. The stylet can be a needle such as a spinal needle. The stylet can be a flexible seal that prevents fluid from escaping the central channel of the plunger and stops the stylet from being depressed too far. The stylet can have a diameter that approximates the internal diameter of the desired needle gauge that will be coupled to the device. The stylet should be a larger gauge than the injection needle so that the stylet can fit in and move through the injection needle. The stylet can be made of metal, plastic, or glass.

In some embodiments, the fluid transfer holes in the fluid exchange chamber are angled upward from an inner surface of the fluid exchange chamber to an outer surface of the fluid exchange chamber. Advantageously, the angled holes allow for fluid to exit the chamber but prevent cells from escaping. In some embodiments, the fluid transfer holes have a smaller diameter on an inner surface of the fluid exchange chamber than on an outer surface. The holes can have a round shape, diamond shape, or other shape.

In some embodiments, the stylet base flange and the plunger flange are connected by a spring or a piston. The connection helps the stylet to move with the plunger when the plunger is depressed and provides a means for the user to control the speed and force of the stylet to prevent damage to the cells.

In various embodiments, the volume of tissue delivered is about 10 to 10,000 $mm^3$ or about 100 to 100,000 $mm^3$ and the volume of tissue to fluid is about 1:10.

In various embodiments, the device delivers tissue for a single injection site for a single treatment. In other embodiments, the device can deliver multiple, measured doses for multiple injections from a single device.

Although specific needle sizes and device dimensions are described in the examples herein, one of ordinary skill in the art can envision modified sizes of the device or components thereof in order to accommodate various tissue types or injection sites.

Examples

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Stem cell treatments have arisen as the future of medicine, and injections of tenogenic neo-tissue grown from adipose-derived mesenchymal stem cells have proven to be an effective method for treatment of tendon injuries (Kim et al., 2017). Because of their ability to proliferate and recruit circulating cells, neo-tissue treatments can lead to complete regeneration which is not possible naturally or with other treatment procedures (Andarawis-Puri et al., 2015). Currently, no injection device or method exists that can transport the neo-tissue into the body while maintaining a sterile environment and without significantly damaging cells. Provided herein is a device that can sterilely store neo-tissue in a liquid growth medium for an extended period of time before injection and then facilitate the injection process while minimizing forces experienced by the tissue to keep the cells viable. The device functions by storing the neo-tissue in a porous fluid-exchange chamber which allows the neo-tissue to interface with the liquid growth medium. A capsule completely encloses the fluid-exchange chamber to prevent contamination. The device undergoes a simple two-part process to inject. First, the plunger expels the excess liquid medium while the needle is outside of the patient. Next, the needle is maneuvered to the injury site, and the stylet pushes the neo-tissue from the device, through the needle, and into the target area. Advantageously, the device is user-friendly, low-cost, sterilizable, and compatible with preexisting systems such as an 18-gauge needle and ultrasound imaging.

One consideration in a device for delivering neo-tissue to in vivo tendon injuries is that the device is operated safely to avoid harming the patient if it fails. Advantageously, the present device addresses one of the biggest safety considerations by maintaining a sterile environment for neo-tissue transport to minimize the risk of infection. Additionally, the device is convenient. The device is easy to transport and be capable of keeping the neo-tissue viable for at least three days. It is capable of treating tendon injuries on different species, so the needle and stylet sizing can be compatible with the anatomical locations of various tendons (Yang et al., 2013). The device is user-friendly, allowing the clinician to operate the injection device with one hand while using an ultrasound in the other hand to guide the injection. Also, the device is compatible with a standard 1.5-inch, 18-gauge needle, and the dimensions reflect anthropometric data so that most clinicians, regardless of hand size, can operate the device.

The device described herein is a singular device to transport and inject viable cells and tissue implants into a subject. Advantageously, the device can maintain viable cells and tissues in culture fluid within the device chamber. The fluid can be ejected prior to attachment of a standard need of any size for tissue or cell injection. Currently, viable cells and tissues are shipped in various containers and must be loaded into standard injection devices, exposing the contents to environmental conditions and increasing the risk for contamination or damage. With the disclosed device, all intermediary steps are obviated for a seamless, sterile administration that is as simple as a routine medical injection.

In general, the device is comprised of four main components: a stylet, a plunger, a fluid-exchange chamber, and a capsule (also referred to as a shell). The capsule is a cylindrical body with a threaded base that allows for the fluid-exchange chamber to be tightly secured within. In some embodiments, the fluid-exchange chamber is a conical part with a cylindrical base. The chamber contains holes in its walls to facilitate fluid exchange. In some embodiments, the holes can be diamond-shaped. In other embodiments, the holes can be circular. The fluid-exchange chamber can fit snugly within the capsule due to its cylindrical base and its threading. The male Luer lock on the chamber allows for a needle (e.g. an 18-gauge) to be attached at the end of the device. The plunger contains a thumb piece and a spring to facilitate the pushing down movement. The end of the plunger is tapered and can contain a rubber seal ring to avoid damaging the tissue. The stylet is able to fit within a channel in the plunger and is pushed down using the stylet base. In some embodiments, the stylet itself is a modified spinal needle with a rounded base that will guide the neo-tissue into the needle.

In general, the chamber is filled with neotissue and fluid transport medium. When depressed, the plunger expresses the transport medium from the chamber without expelling the neotissue. The plunger includes a rubber stopper or gasket to avoid accidental expulsion of the cell constructs or tissue product. A second plunger, referred to as the stylet plunger, has a stylet attached to the lower end. The stylet plunger is inserted into a channel in the main plunger. This stylet is metal in some embodiments. The stylet advances the cell constructs or neotissue into the injection site. There can be a rubber stopper or gasket on the stylet to prevent the stylet from entering the target tissue.

Figure 1B:
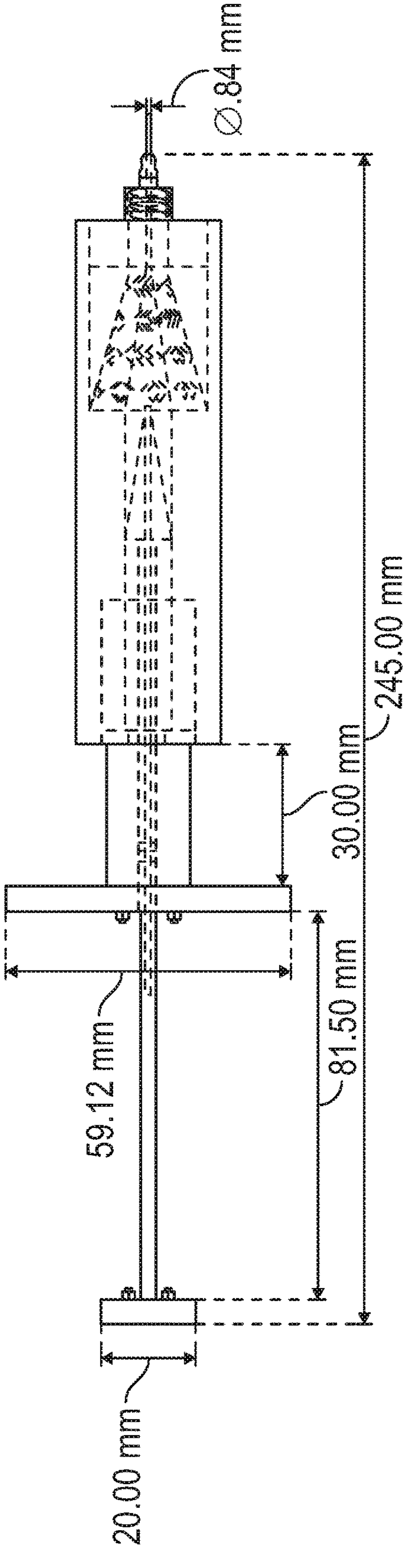
Figure 1C:
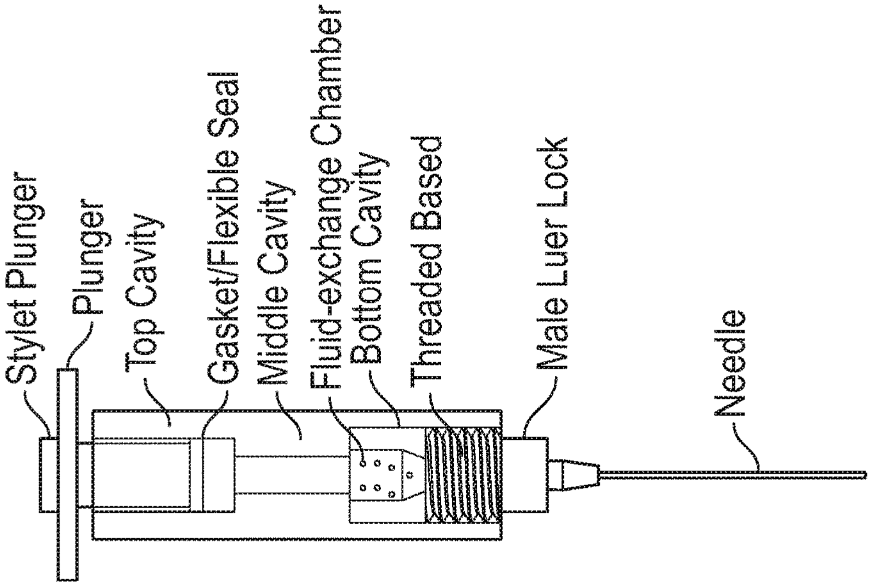
Figure 1D:
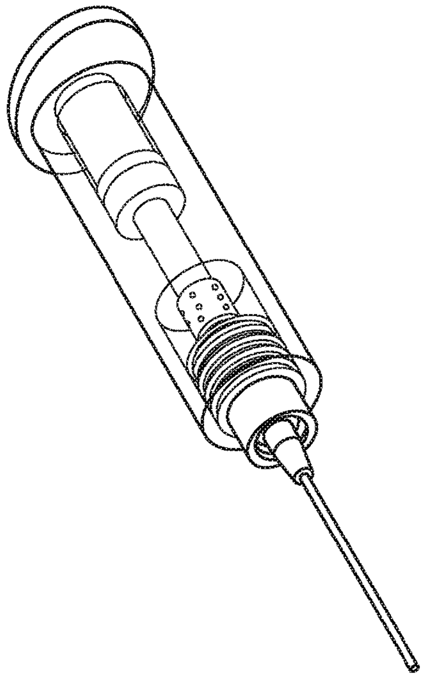
Figure 1E:
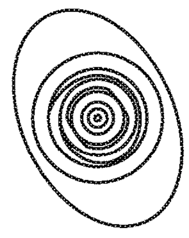
Figure 1F:
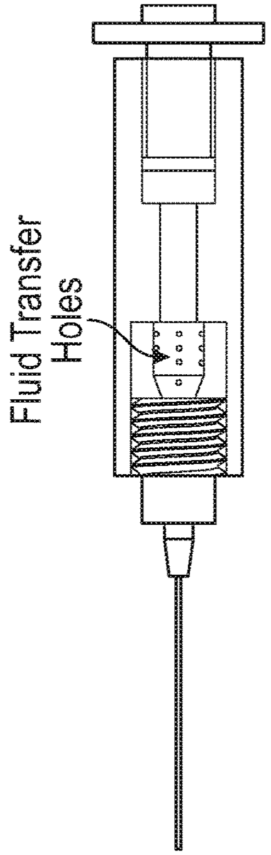
FIG. 1F is a side view.

FIGS. 1A-1E are illustrations of embodiments of the device. FIG. 1A illustrates the path of the plunger and stylet plunger. FIG. 1B is a labeled side view. FIG. 1C is a perspective view. FIG. 1D is a top view showing the plunger, and FIG. 1E is a side view. In general, the assembled device is comprised of nine major parts and a Luer lock cap or 18-gauge needle that are interchanged depending on the intended use of the neo-tissue injection device at the time. Starting on the left of FIG. 1A, the stylet base fits inside of a negative extrusion going through the middle of the plunger, and it has a rubber ring and the stylet attached to its right end. The plunger also has a rubber ring which keeps it inside of the capsule. Moving to the right of the diagram, the conical (funnel-shaped) part of the plunger fits within the funnel-shaped fluid-exchange chamber which sits in an open space in the capsule and has the Luer lock attached to its smaller end. Although not pictured in the model, a spring can wrap around the rod part of the stylet base and reside between the flange of the stylet base and flange of the plunger. The light grey areas in the figure show the final positions of the plunger and stylet when depressed. FIGS. 1B-1E show various views of the device.

Before use, the neo-tissue injection device can be in two separate assemblies: 1) the plunger, stylet base, their respective rubber rings, the stylet, and the spring; and 2) the capsule, fluid-exchange chamber, and Luer lock together. At this point, the Luer lock should also be blocked off with a standard Luer lock cap. First, the neo-tissue and fluid medium can be loaded into the fluid-exchange chamber by inserting them through the open end of the capsule, and then, the plunger assembly group is attached to this end to seal the capsule and maintain an airtight, sterile environment. The device and neo-tissue within can be sterilely stored providing the assembly stays together and the cap remains on. The storage time can be such as up to three days, or a time for which the tissues can survive in the medium.

When it is time to inject the subject with the neotissue, the Luer lock cap is replaced with an needle (e.g., an 18-gauge needle or other gauge appropriate for injecting the material without damage). Next, the plunger is pushed to expel excess fluid from the chamber. Depending on the preferences of the clinician, the needle can be removed from the Luer lock and inserted into the injury site with the assistance of ultrasound imaging, or the needle with the rest of the assembly still attached can be moved to the injury site also with the use of ultrasound imaging. This option exists because some clinicians may find it easier to maneuver a small, singular needle to the target area rather than the entire assembly. Additionally, the excess fluid in the chamber can be expelled directly after removing the Luer lock cap from the device, and the needle can be placed at the lesion site without first attaching it to the device. This approach would cause a small volume of air, rather than transport fluid, to reside inside the needle prior to injecting the neo-tissue. If necessary, the rest of the device is reattached to the needle before the stylet base is advanced to inject the neo-tissue into the injury site. Finally, the needle and device are removed and properly disposed of.

Fluid-Exchange Chamber:

Moving to the fluid-exchange chamber, this part can consist of a funnel, a pre-injection chamber (or pre-injection tube) under the small end of the funnel, and a threading disk around the pre-injection chamber. The three sections function together to hold the neo-tissue in a sterile space where it can interact with an adequate amount fluid medium and later be easily advanced into the Luer lock, through the needle, and finally into the injury site.

In some embodiments, the funnel part of the fluid-exchange chamber can have rows of holes positioned around its circumference, (e.g., about 1.5 mm apart). The holes can be diamond shaped, where the inner diamonds are smaller, and each one connects to a larger outer diamond that is positioned slightly higher, causing the holes to slope upwards from the inside to the outside. This incline helps prevent the tissue from slipping out of the fluid-exchange chamber and into the capsule space on its own and when the plunger is pushed forward to expel fluid medium. In other embodiments, the holes can be circular, ovoid, or other shape.

In an example, if the neo-tissue is cut to a predetermined size of 4 mm long with a diameter of 0.838 mm or larger, it should not be able to exit the fluid-exchange chamber because the inner diamonds are too small. The diamonds are enlarged on the outside so that there is more space for fluid to move in and out of the funnel. In particular embodiments, diamonds can be used instead of circles because it is more difficult to 3D print round shapes. Alternatively, the holes may be drilled.

Figure 2B:
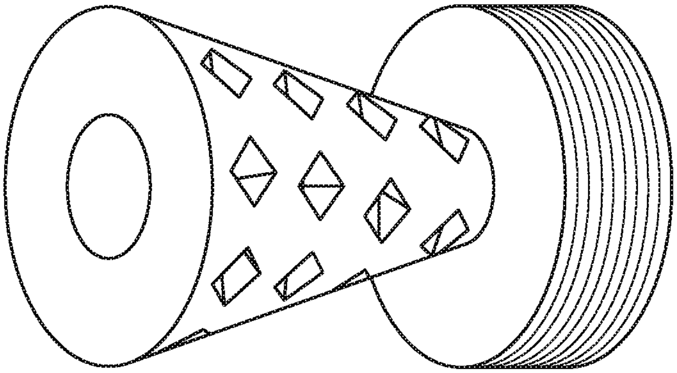
FIG. 2A is an illustration of the fluid-exchange chamber and FIG. 2B is an illustration of the fluid-exchange chamber including threading in accordance with embodiments of the present disclosure.
Figure 2A:
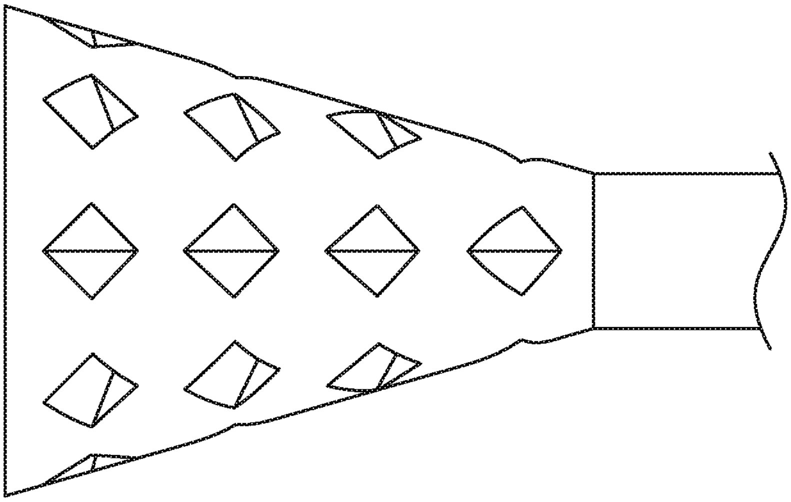

In embodiments, the lower part of the fluid-exchange chamber is conical or funnel-shaped to facilitate the initial loading of the neo-tissue and fluid growth medium (FIG. 2A). With a larger top diameter, there is less risk of the user forcing the fragile neo-tissue into a small space, which could damage the tissue and reduce cell viability. Thus, the neo-tissue can easily be dropped into the device and then naturally moves towards the smaller end of the funnel, circumventing the issue of excessive needle poking and manipulation in previous injection methods. The inside space of the funnel shape is large enough so that the neo-tissue can freely move within the space and all surfaces of the neo-tissue can interact with the fluid growth medium whereas a smaller or tighter tube may hold the tissue in place and prevent parts of the neo-tissue from being nourished by the liquid medium. Aside from easier loading and space for fluid exchange, the funnel shape assists in easing the tissue towards the smaller diameter pre-injection chamber at the smaller end of the funnel. The top of the funnel is blocked off by the ends of the plunger and stylet, so the neo-tissue can float freely within the open space of the funnel, and avoiding shear stresses from contact with the walls when it is being pushed down by the plunger.

The pre-injection chamber is a straight tube section at the exit of the fluid-exchange chamber. The tissue is contained here for the short period of time after the plunger has been moved to expel excess liquid growth medium and before the stylet is used to inject the neo-tissue. In embodiments, it has the same diameter as an 18-gauge needle, so once the neo-tissue has been pushed into the pre-injection chamber by the plunger, it is a straight-line path from through the Luer lock, needle, and out of the device. The length of the pre-injection chamber can be slightly longer than the length of the neo-tissue to allow for some fluid to move with the tissue and act as a surface fluid that will reduce shear stresses and be injected with the neo-tissue to offer post-injection nourishment in the harsh wound environment.

Figure 2C:
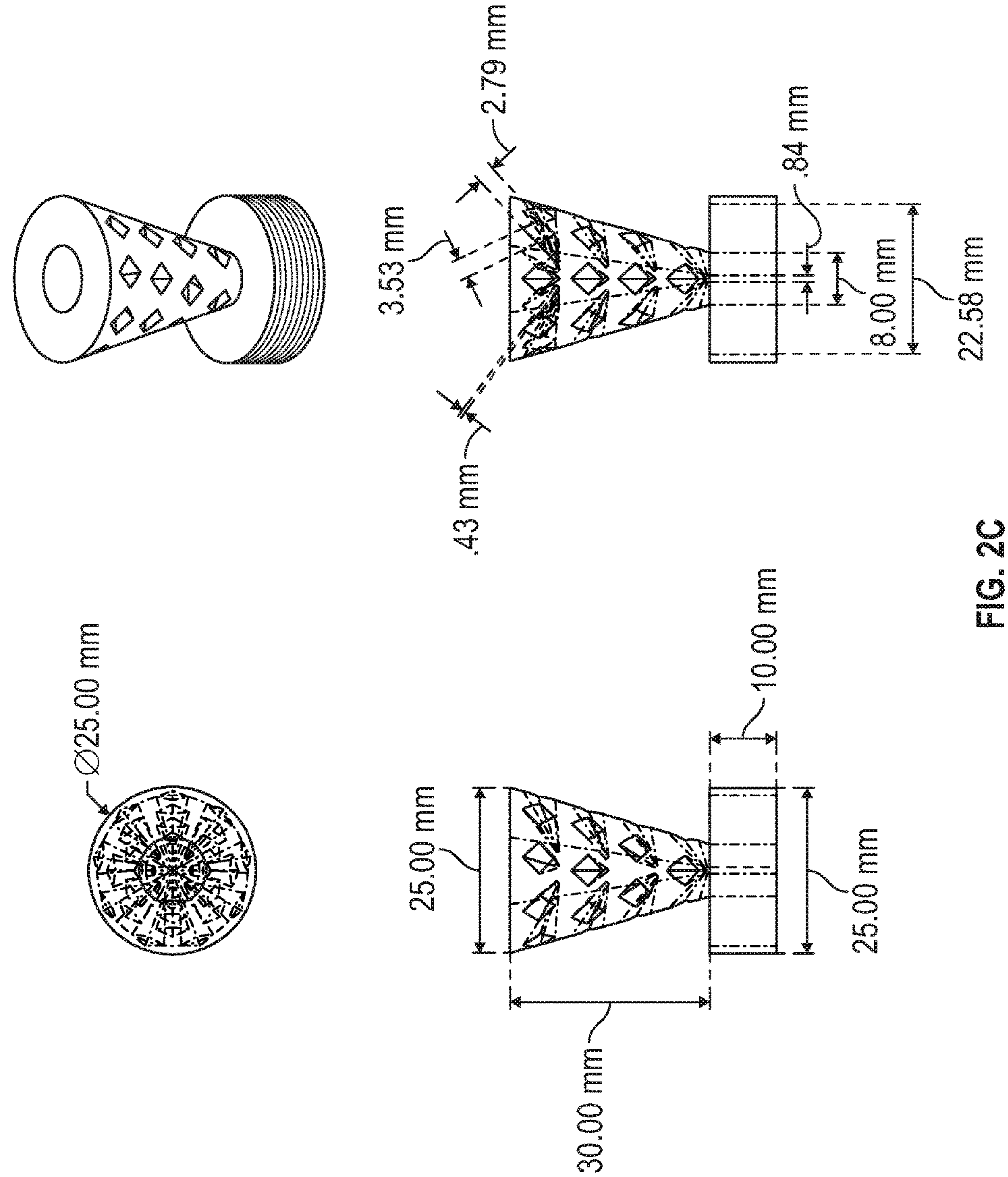
FIG. 2C provides a dimensioned drawing of the fluid exchange chamber that is conical and has diamond-shaped holes in accordance with embodiments of the present disclosure.
Figure 2D:
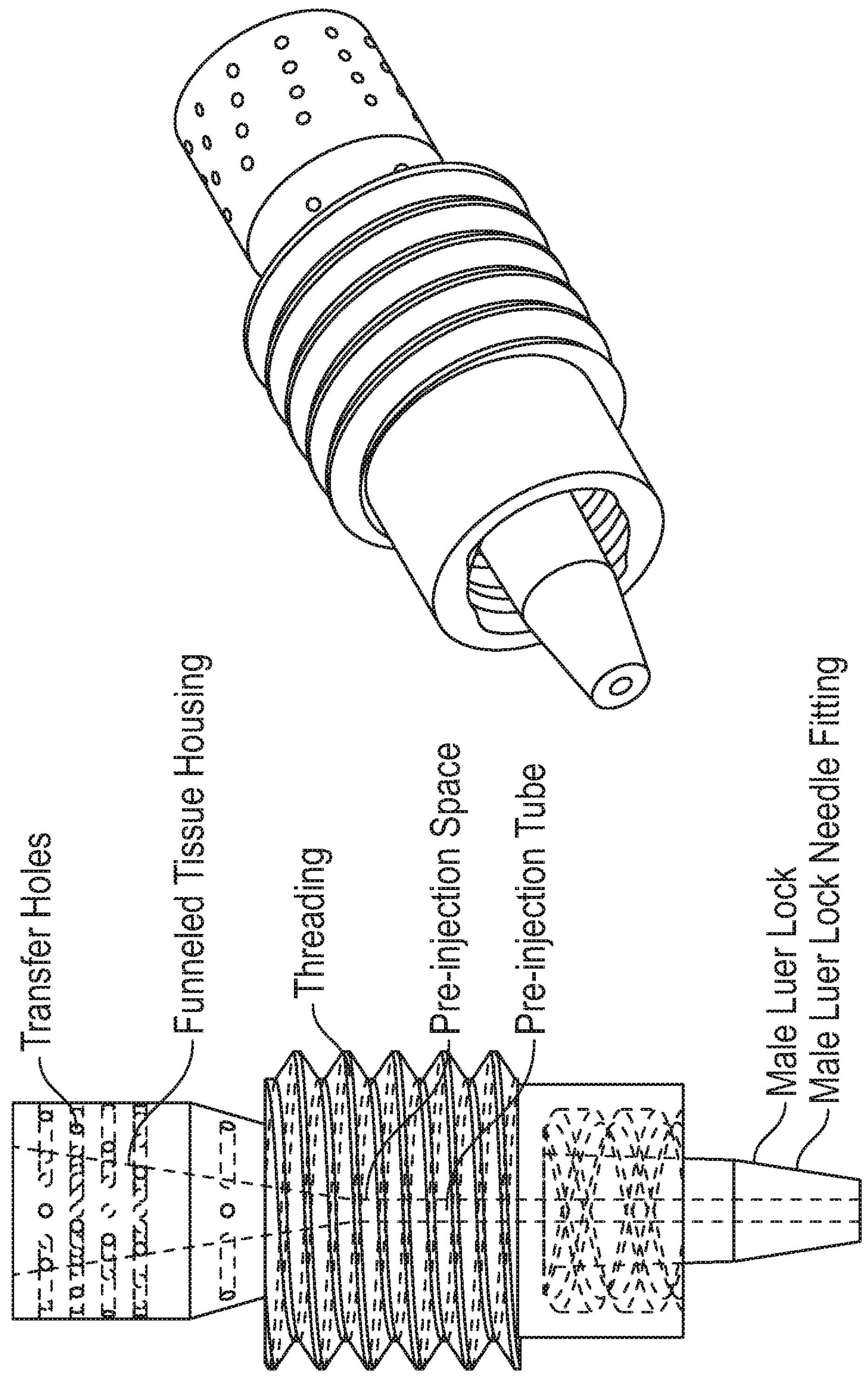
FIG. 2D is a dimensioned drawing of the fluid exchange chamber fitted with a Luer lock.
Figure 2E:
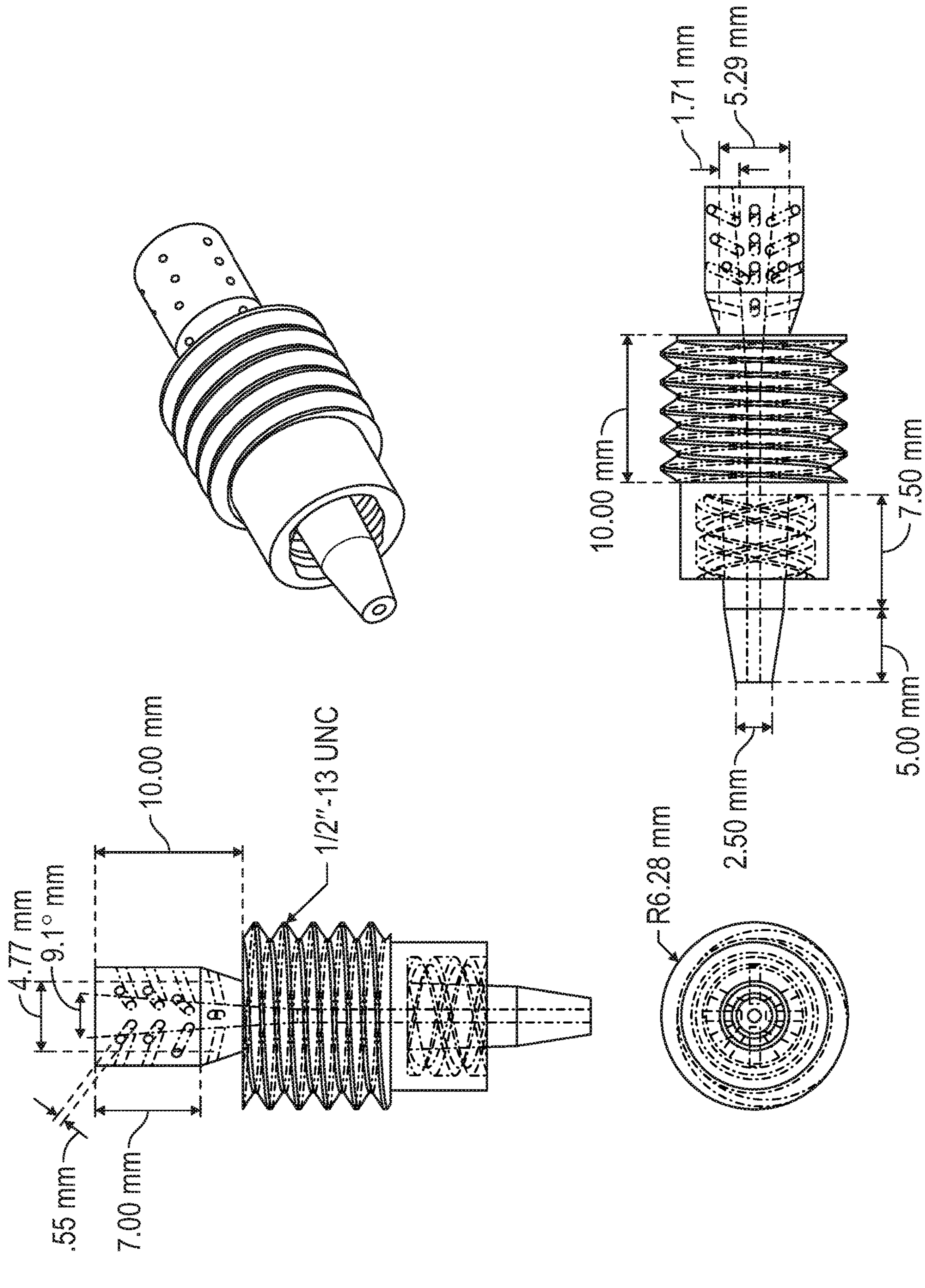
FIG. 2E is a dimensioned drawing of an embodiment of the fluid-exchange chamber that is conical in shape circular holes and fitted with a Luer lock.
Figure 2F:
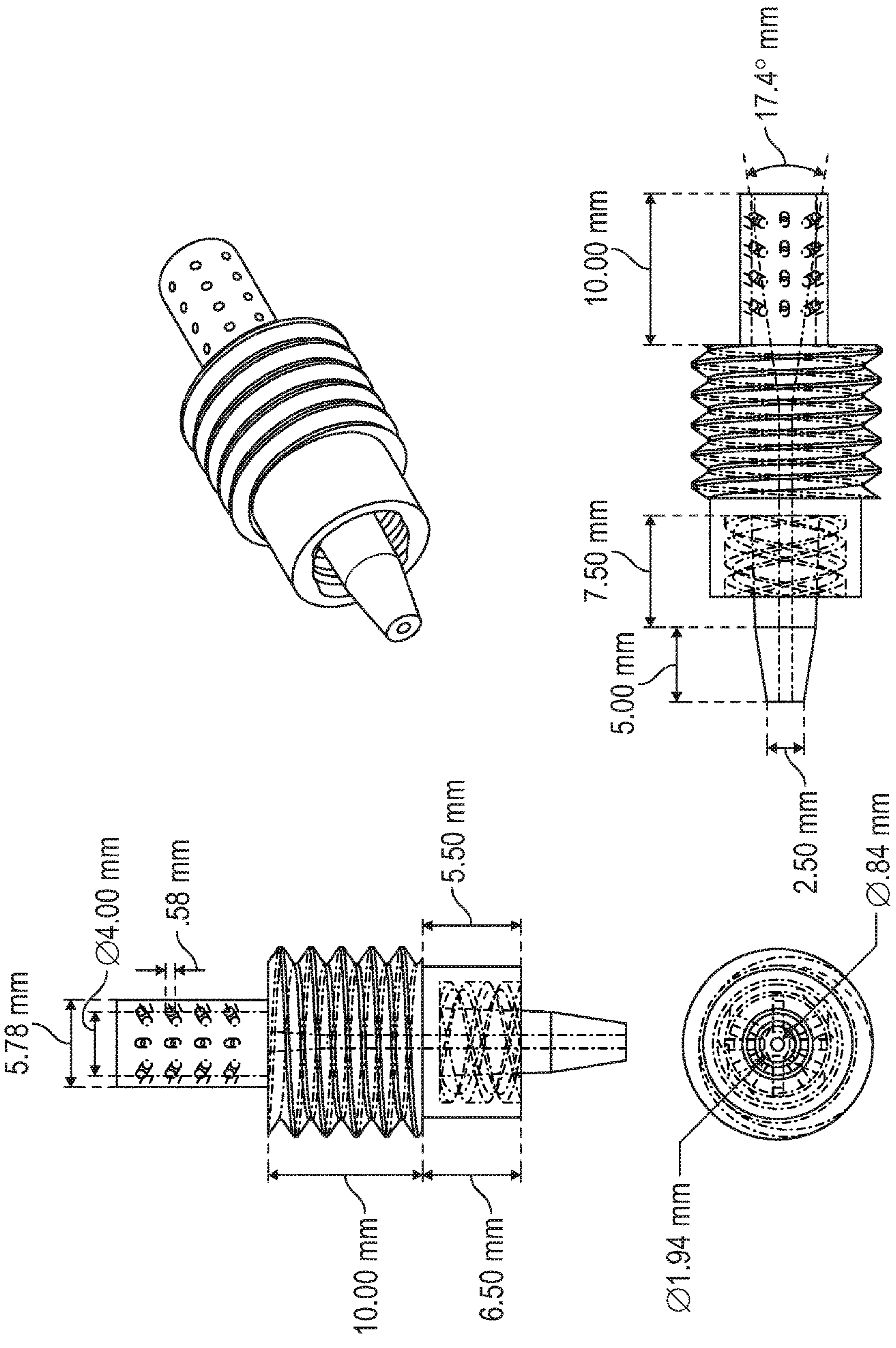
FIG. 2F is a dimensioned drawing of an embodiment of the fluid-exchange chamber that is cylindrical in shape with a funneled portion at the bottom and fitted with a Luer lock.

The fluid-exchange chamber can also comprise a ring of threads having the same height as the pre-injection chamber which it completely surrounds (FIG. 2B). It has the same diameter as the inner diameter of the bottom part of the capsule, and the two parts have complementary threading that allow them to be attached together in an airtight manner. FIG. 2C provides a dimensioned drawing of the fluid-exchange chamber and FIGS. 2D-2F illustrate the fluid-exchange chamber fitted with the Luer lock. In some embodiments, as shown in FIG. 2F, the fluid-exchange chamber is cylindrical in shape, having a funneled portion at the bottom.

Figure 3A:
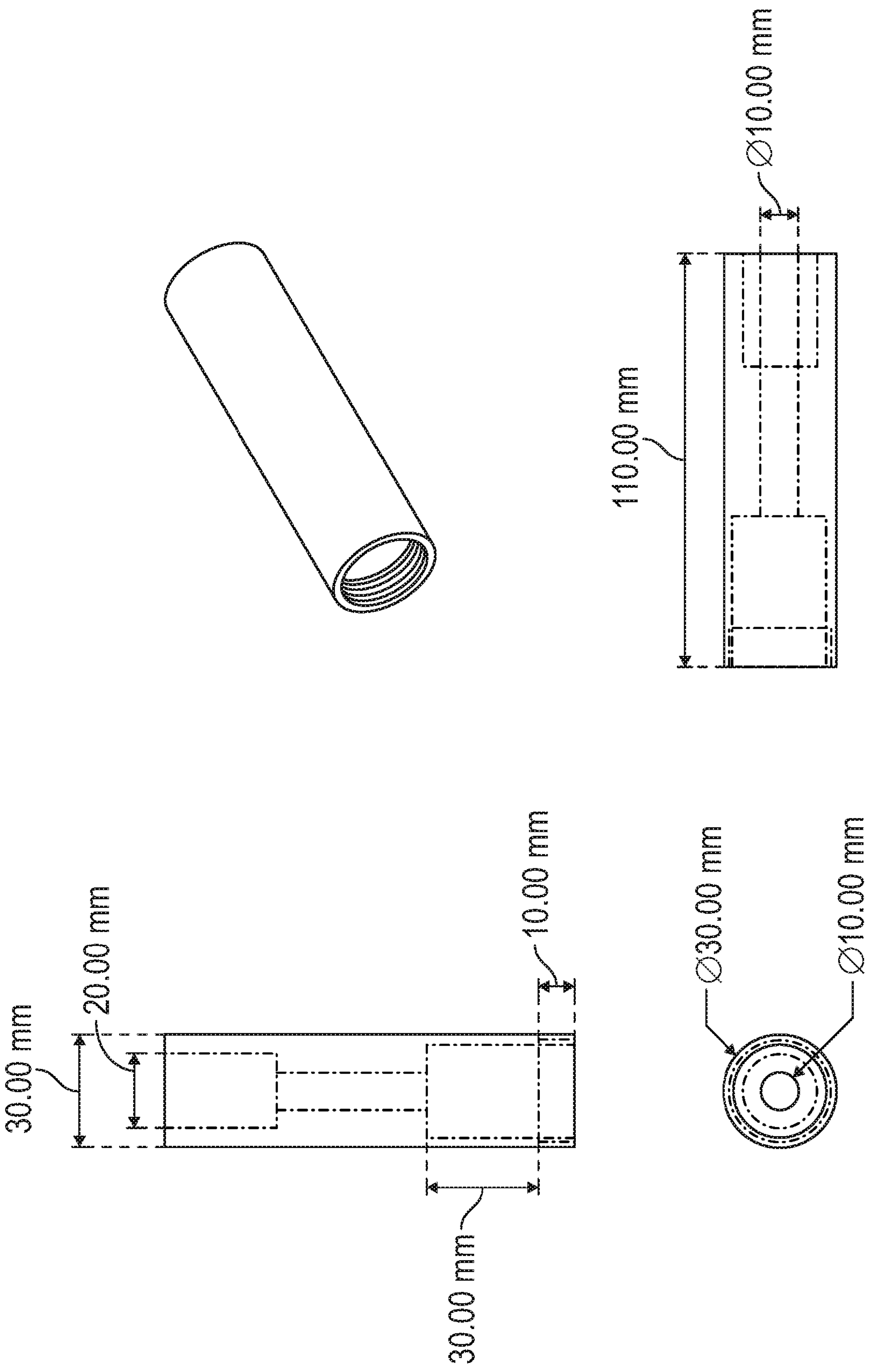
FIGS. 3A-3C are dimensioned drawings of the capsule having a threaded portion in accordance with two possible embodiments of the present disclosure.
Figure 3B:
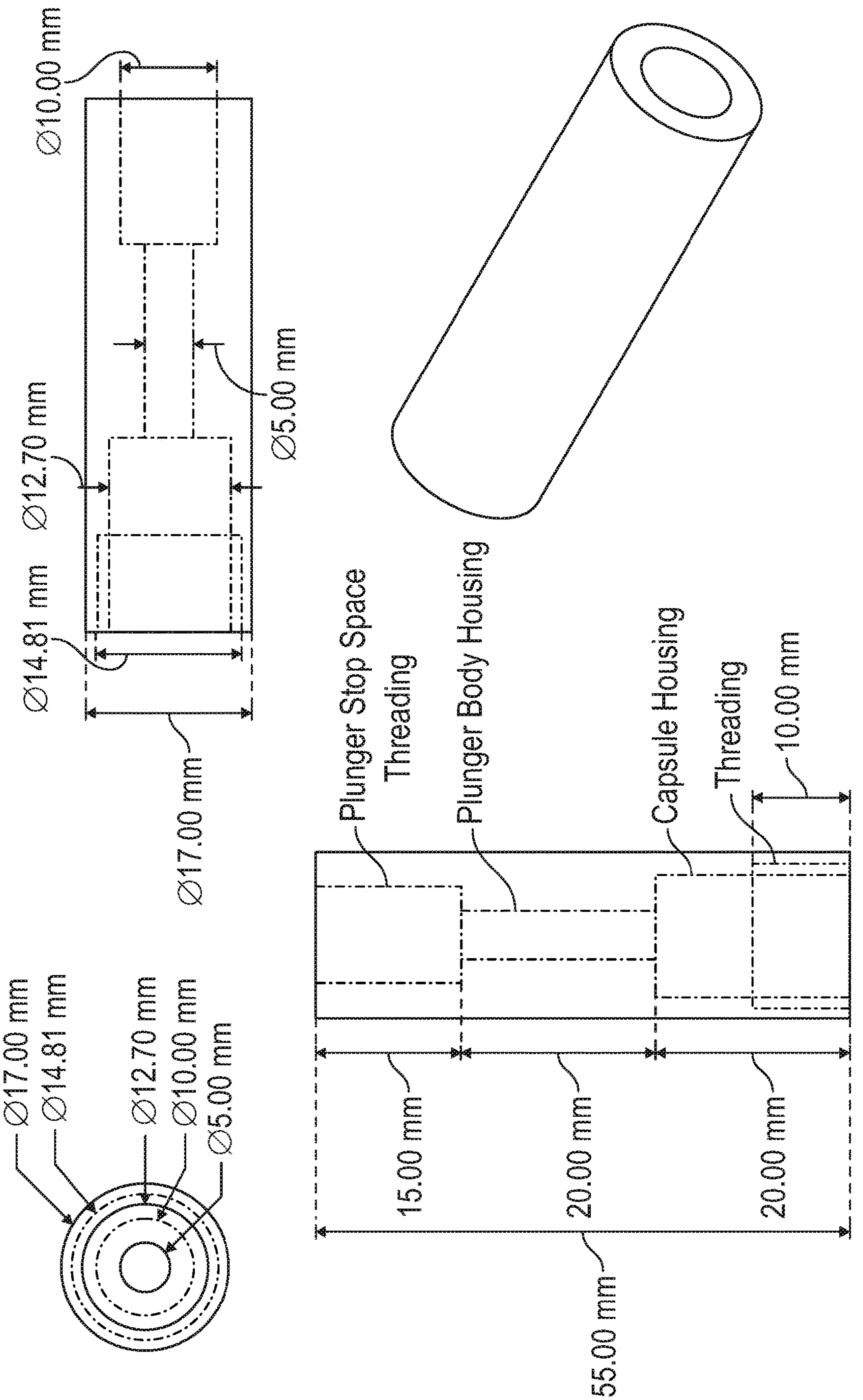

Capsule:

The capsule, or outer shell, forms the exterior of the device. It is essentially a long cylinder with three different levels of internal cavity. In the embodiment shown in FIG. 3A, the outer diameter is 30 mm and the height is 110 mm. In the bottom level, there is a 25 mm cavity that extends from the base up to 40 mm to receive a fluid exchange chamber as shown in FIG. 2C. The bottom 10 mm is threaded, and this is where the base of the fluid-exchange chamber will screw in. In some embodiments, the threading is an ISO metric M28×3 with a 0.2 mm flank offset. This level of the capsule will house the fluid-exchange chamber and extra transport fluid will be contained between the walls of the capsule and the fluid-exchange chamber. The embodiment shown in FIG. 3B corresponds to a fluid exchange chamber having dimensions as shown in FIG. 2F. The embodiment in FIG. 3C corresponds to the fluid exchange chamber in FIG. 2E.

The middle level of the capsule has a cavity with an inner diameter of 10 mm and 40 mm in length. This region will contain the conical portion of the plunger before injection. When the plunger is pushed down, the cylindrical portion of the plunger will fill the entire space, as the conical portion will be inside of the fluid-exchange chamber within the bottom level of the capsule.

Figure 3C:
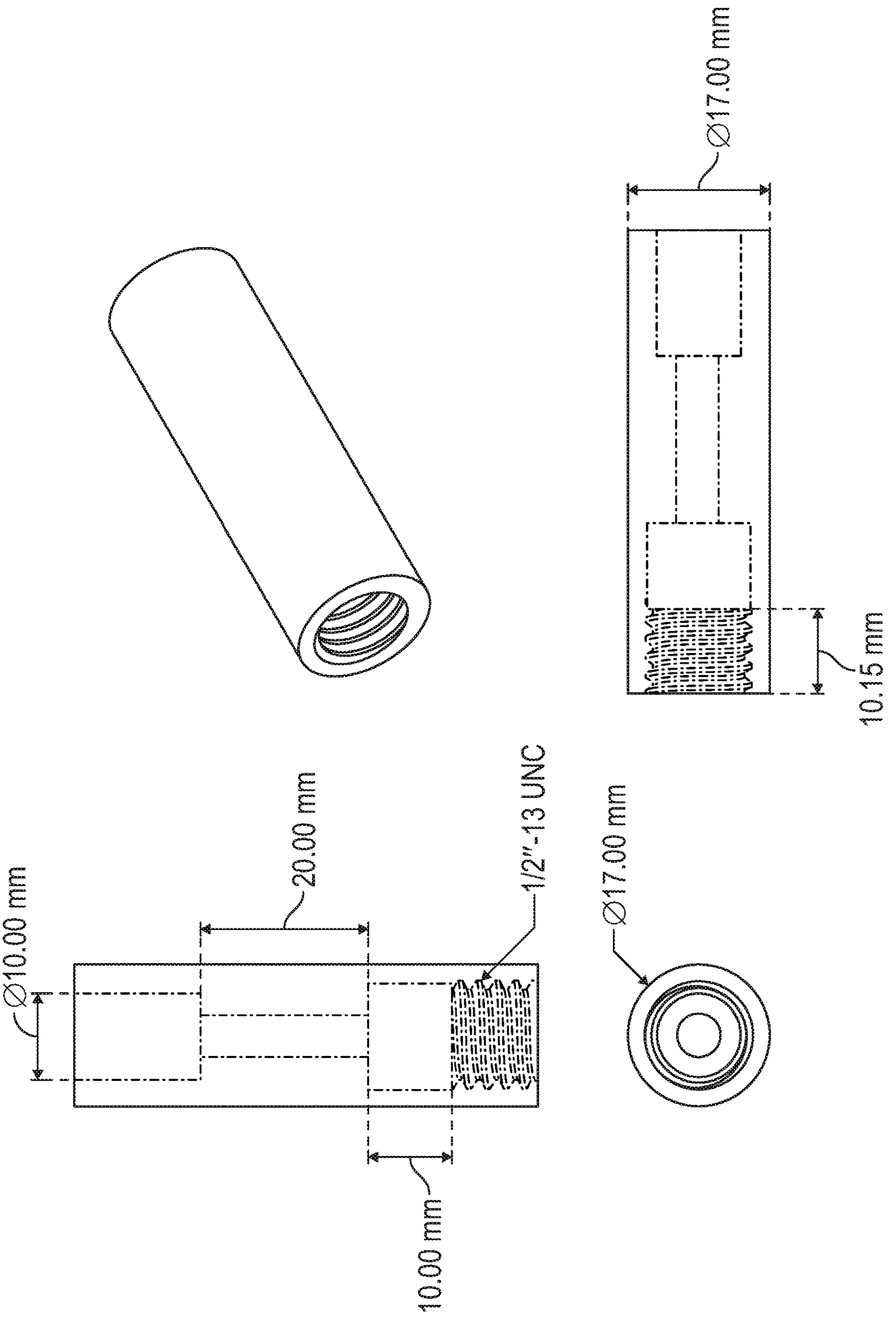

The cavity in the top level of the capsule spans the remaining distance of 30 mm with an inner diameter of 20 mm. This section receives the top portion of the plunger and the rubber ring for the plunger. When the clinician pushes the plunger down, the plunger slides downwards, and the motion is stopped when the rubber ring around the plunger meets the edge where the second and third levels of the capsule meet. The motion of the plunger is stopped because the inner diameter drops from 20 mm to 10 mm at the edge where the second and third levels meet. At this point, the plunger has reached the base of the fluid-exchange chamber, and the neo-tissue is at the base of the pre-injection channel. Now, the clinician can prepare to push the stylet down to complete injection of the neo-tissue into the lesion site. FIG. 3C shows another embodiment of a threaded capsule having different dimensions.

Figure 4A:
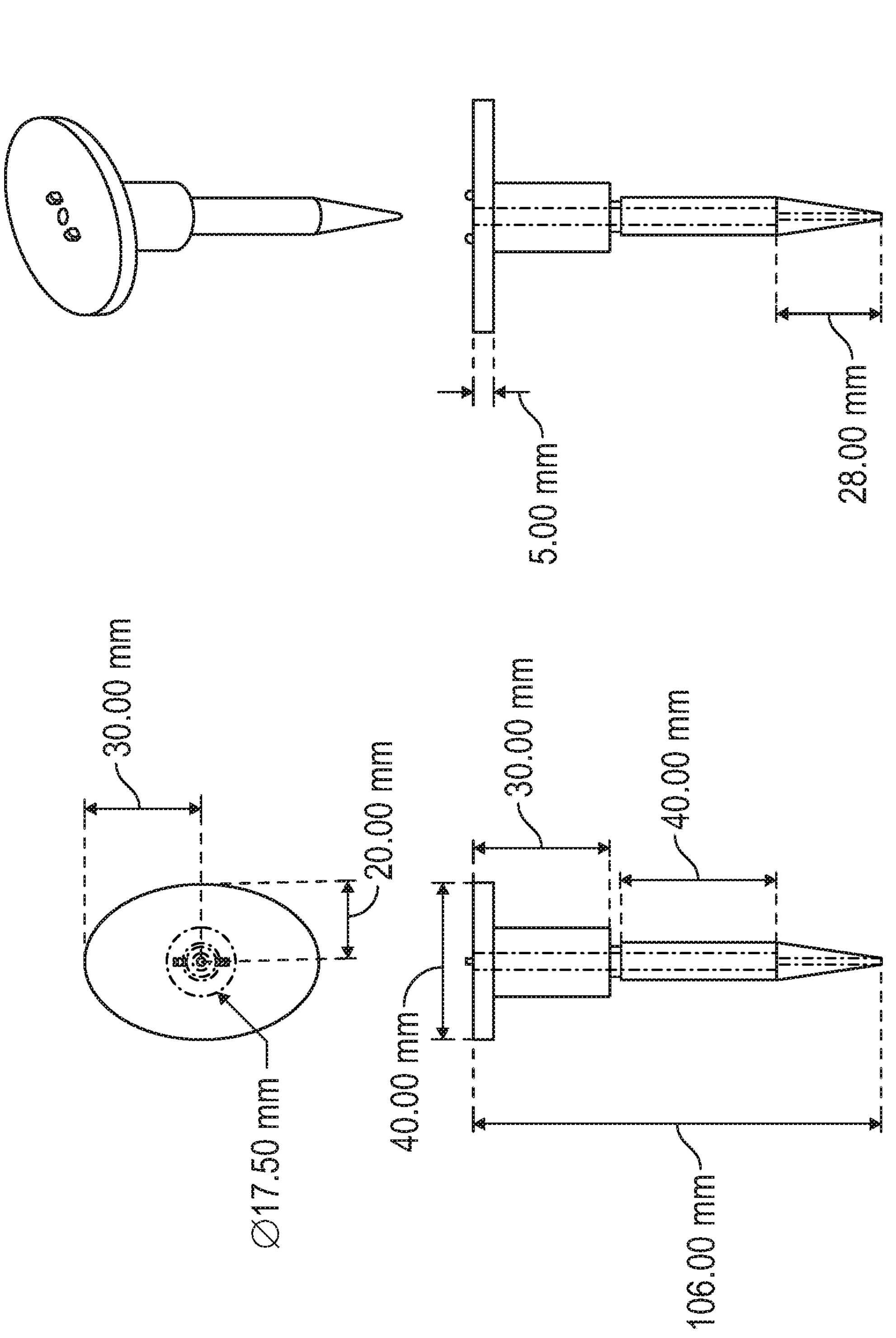
FIGS. 4A-4D are dimensioned drawings of the plunger in accordance with two possible embodiments of the present disclosure.
Figure 4B:
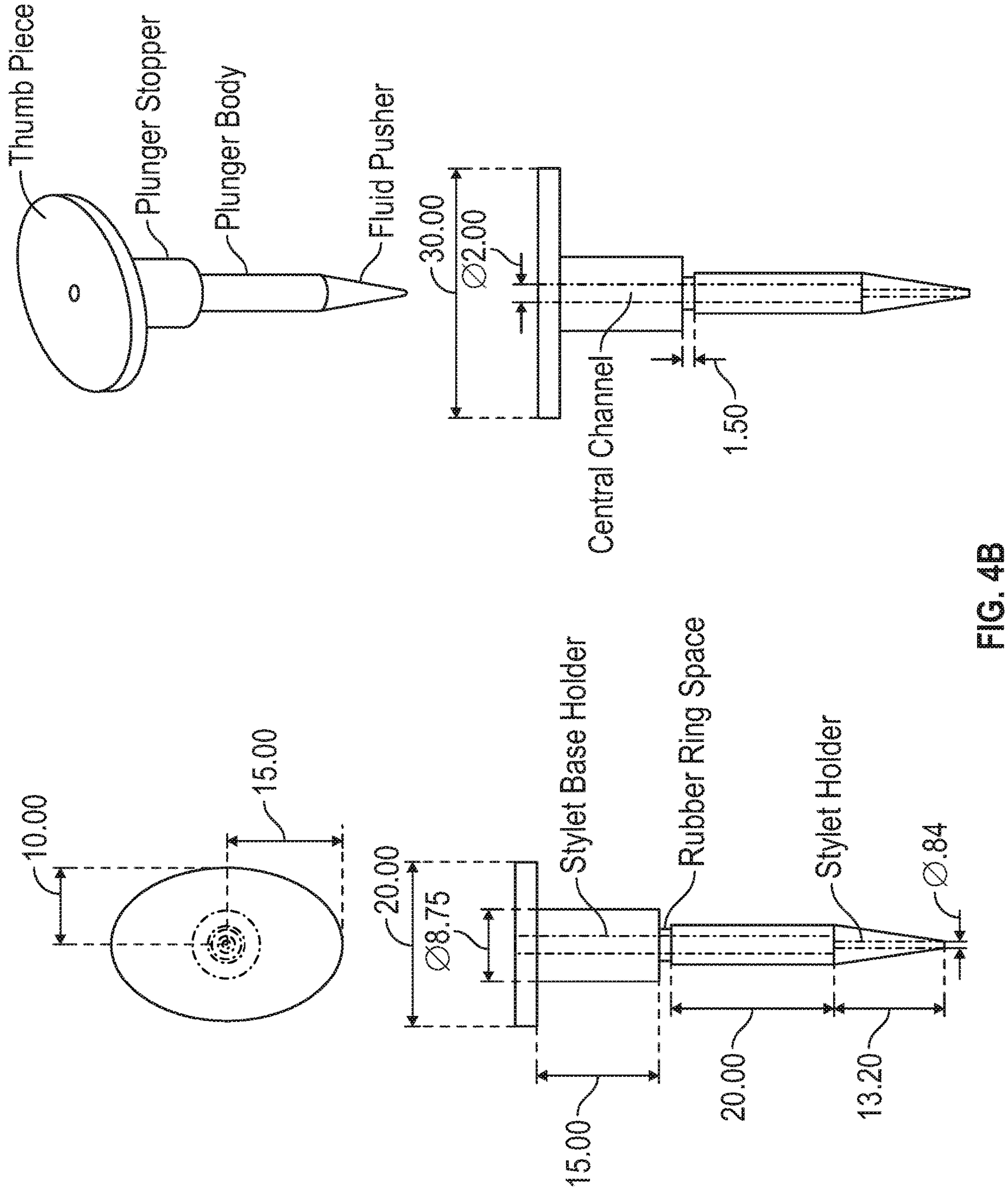
Figure 4C:
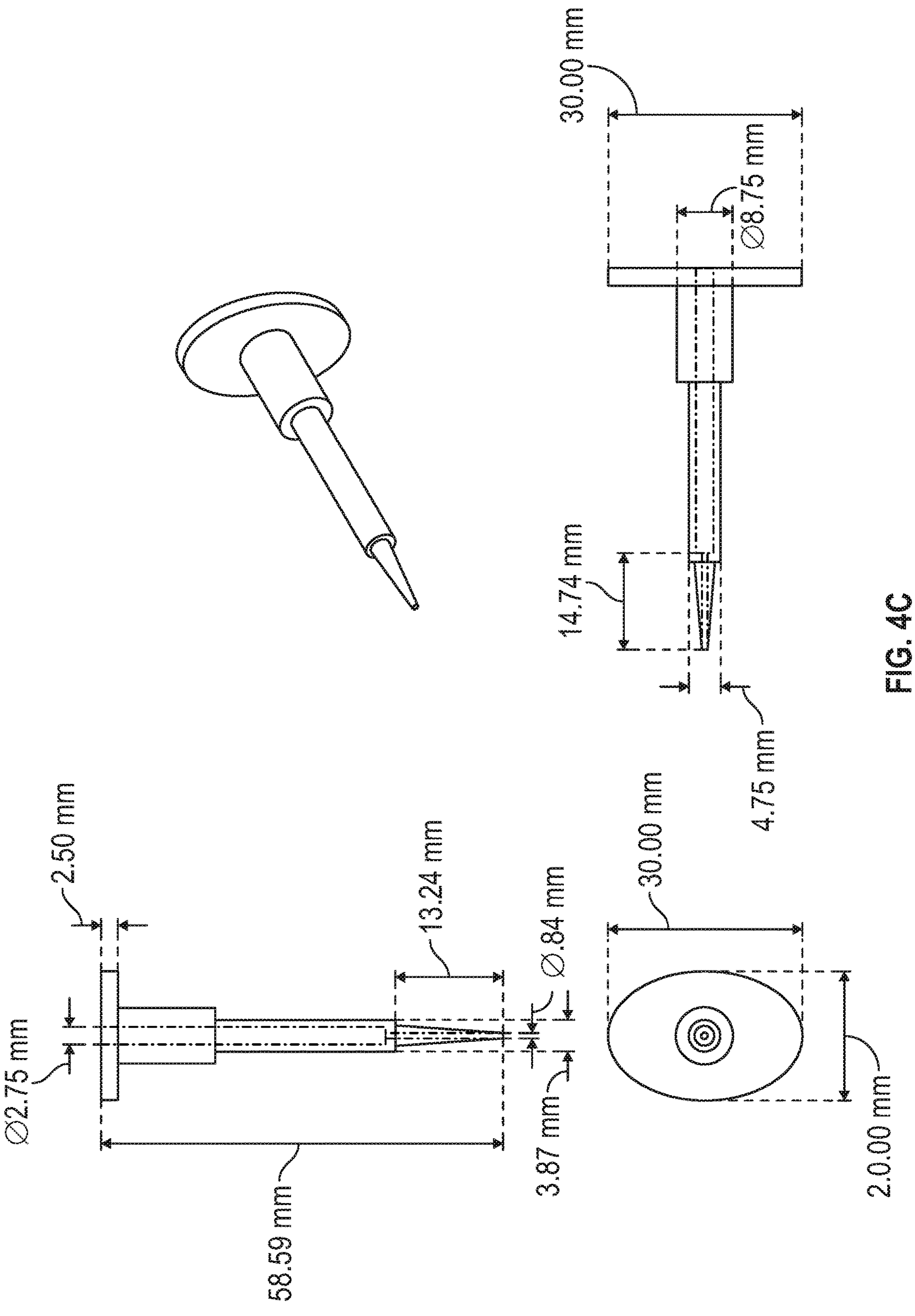
Figure 4D:
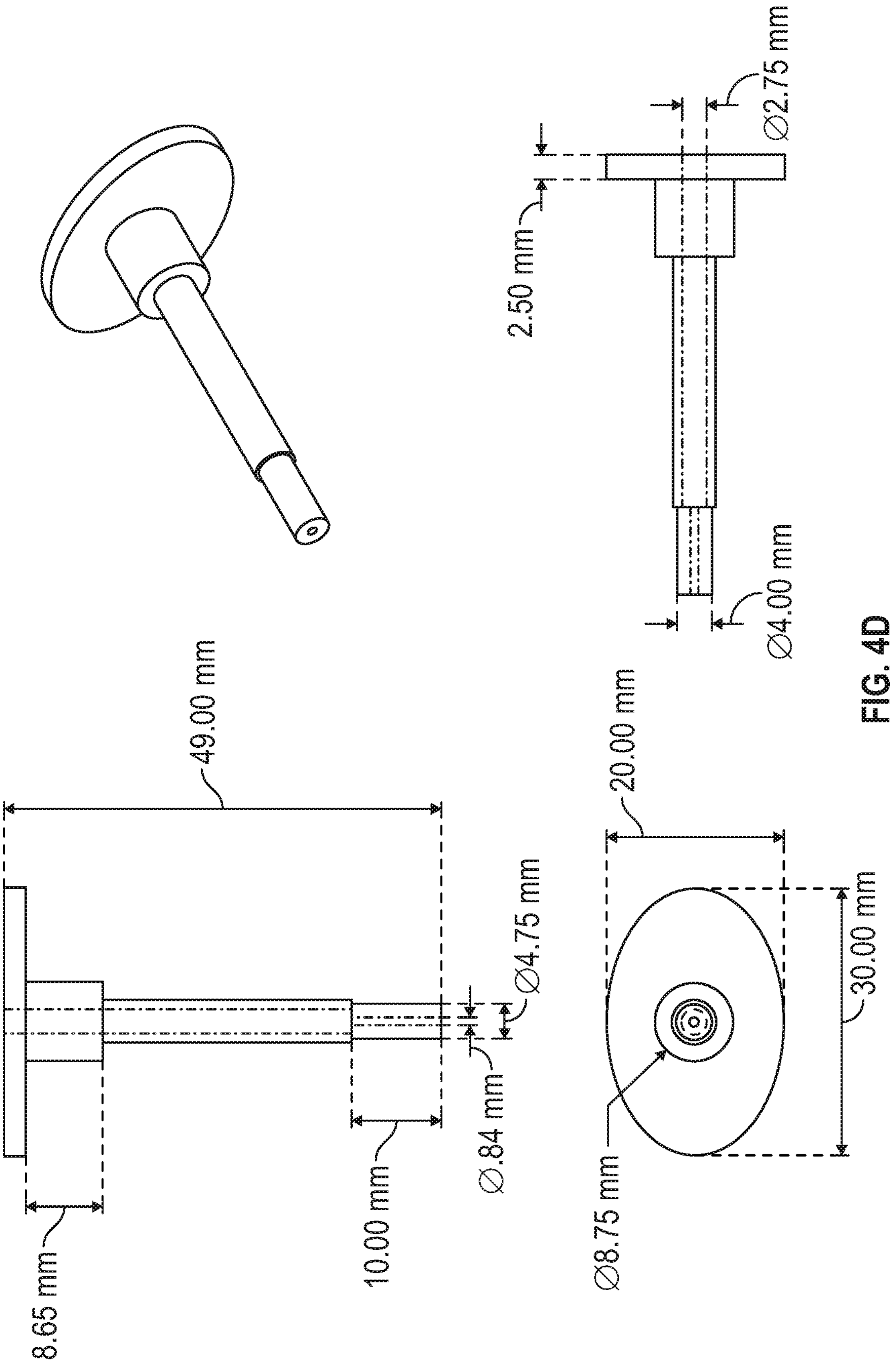

Plunger:

The plunger serves as a cap for the larger end of the fluid-exchange chamber before injection to keep the space airtight and sterile (FIGS. 4A-4D). When pushed down, the plunger expels the fluid out of the funnel and gently moves the neo-tissue into the pre-injection chamber. The plunger in FIG. 4A is dimensioned to fit with the shell in FIG. 3A, while the plunger in 4C is dimensioned to fit with the shell in FIG. 3C. The plunger shown in FIG. 4D is dimensioned to: correspond to the shell in FIG. 3C and the fluid exchange chamber in FIG. 2F.

In some embodiments; an ellipsoid flange at the top allows users to more easily push the plunger down. The flange also serves as a surface on which loops can be placed for a spring. Attached to the flange is a thick shaft that has a compressible (e.g., rubber) ring at the bottom of it. In some embodiments, groove or shelf can hold the ring. The diameter of this thicker section prevents the plunger from moving through the middle section of the capsule and ensures that the plunger stops at the appropriate spot. The next part of the plunger is a thinner section which fits in the center space of the capsule. The conical tip of the plunger is the same shape as the inside space of the fluid-exchange chamber, allowing it to expel all fluid in the funnel when the plunger moved down.

The center of the plunger contains a negative extrusion, or channel, to receive the stylet and stylet base. The channel diameter in the body is slightly larger than the diameter of the stylet base. The channel narrows in the conical portion, having a diameter slightly larger than the diameter of the stylet. The complementary diameters of the parts and spaces keep the device airtight and sterile when paired with the rubber pieces, and the change in diameter will force the stylet base and stylet to stop at the appropriate spots when they are pushed down to inject the neo-tissue. This prevents the stylet from moving too far and accidentally injecting the neo-tissue into the wrong spot or piercing part of the tendon, causing further injury. The design also ensures that the stylet is moved far enough to eject the neo-tissue from the device.

Stylet Plunger:

The stylet plunger includes a base (FIG. 5A) and a stylet. The stylet base holds the stylet and makes it easier to push the extremely thin and otherwise fragile stylet. The stylet base can have a flange at one end with loops into which the spring can be threaded and crimped and a rod at the other which has a negative extrusion into which the stylet will fit. In embodiments, the extrusion can be filled with adhesive that will tightly hold the stylet when it is inserted. The stylet base fits into the negative extrusion of the plunger. The base can also have a rubber piece to ensure that it stays in place and to seal the device.

The stylet is the piece that will push the neo-tissue through the pre-injection channel and needle attachment. In a particular embodiment, the stylet (not shown) is dimensioned to travel the entire length of the 1.5-inch needle attachment, and to fit inside the negative extrusion or stylet space in the stylet base (FIG. 5B, which is dimensioned to correspond to the plungers in FIGS. 4C and 4D). In this embodiment, the stylet length is 123.60 mm long with an outer diameter of 0.718 mm. In the prototype design, the stylet was created by cutting a 7-inch spinal needle to the desired length with a bandsaw and the open ends of the needle closed by powder welding or filling them with epoxy.

Figure 6:
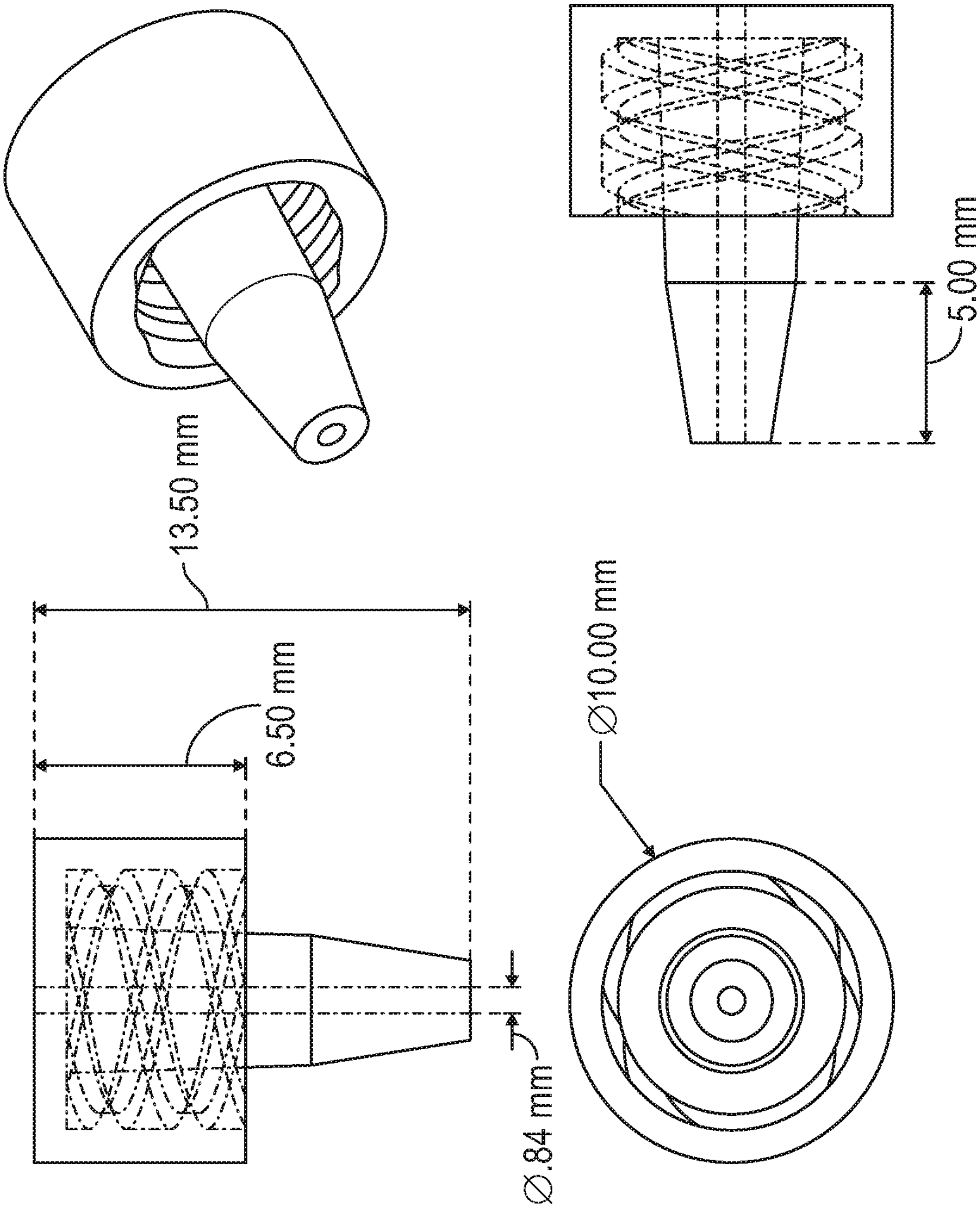
FIG. 6 is a dimensioned drawing of the male Luer lock in accordance with embodiments of the present disclosure.

Luer Lock:

The Luer lock attaches a standard needle to the device. In embodiments, the Luer locks are compliant with ISO 80369-7 which is set by the International Organization for Standardization (ISO). To ensure compliance with the standards, the Luer lock used in the present example (FIG. 6) was created with the Luer lock extension in Autodesk Fusion 360. A male Luer lock with a 0.838 mm hole diameter was created, and then a 10 mm extrusion was added to account for the space in the needle hub between the end of the Luer lock and the base of the needle.

Figure 7A:
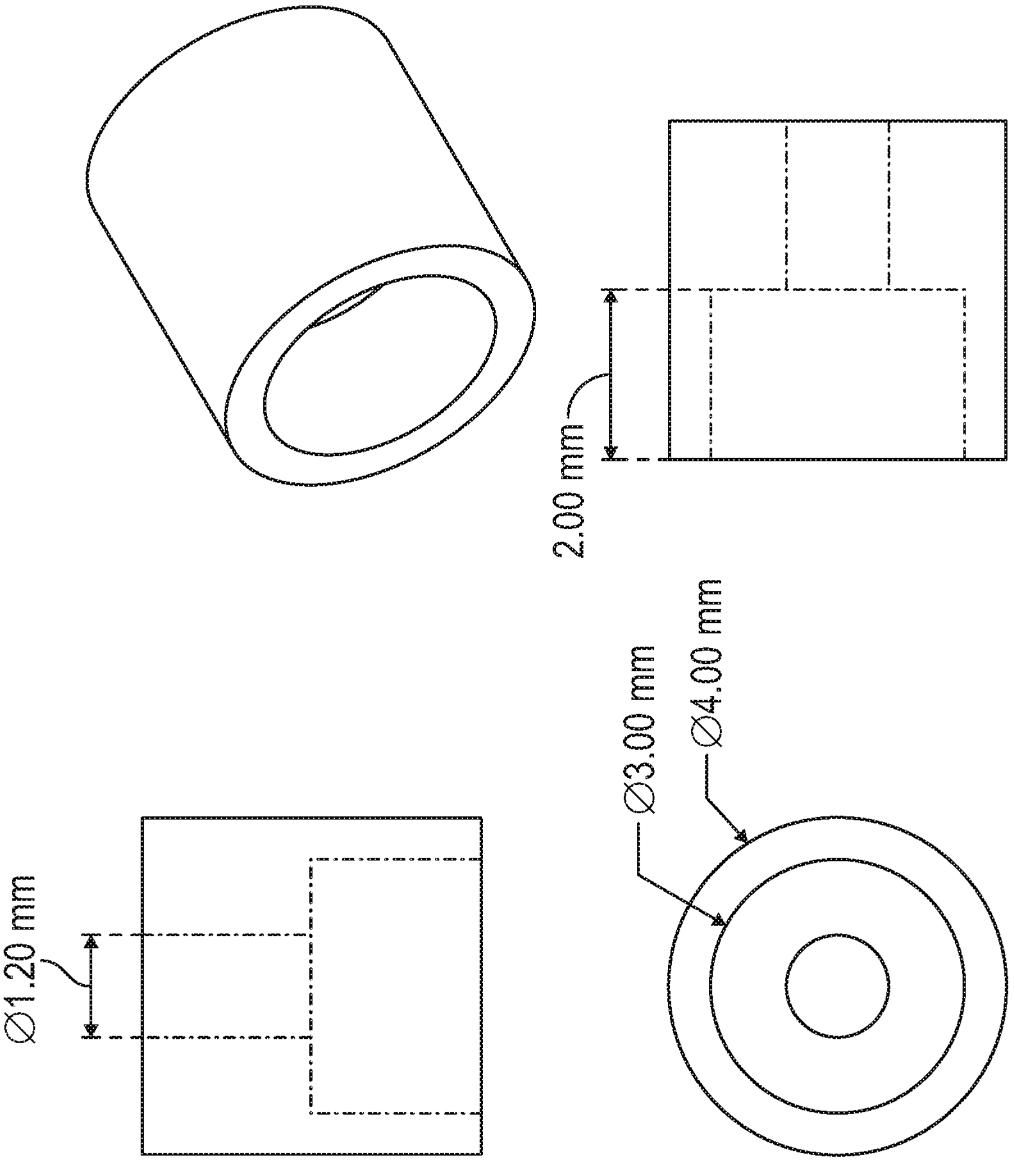
FIGS. 7A and 7B are dimensioned drawings of the rubber ring for the stylet base.
Figure 7B:
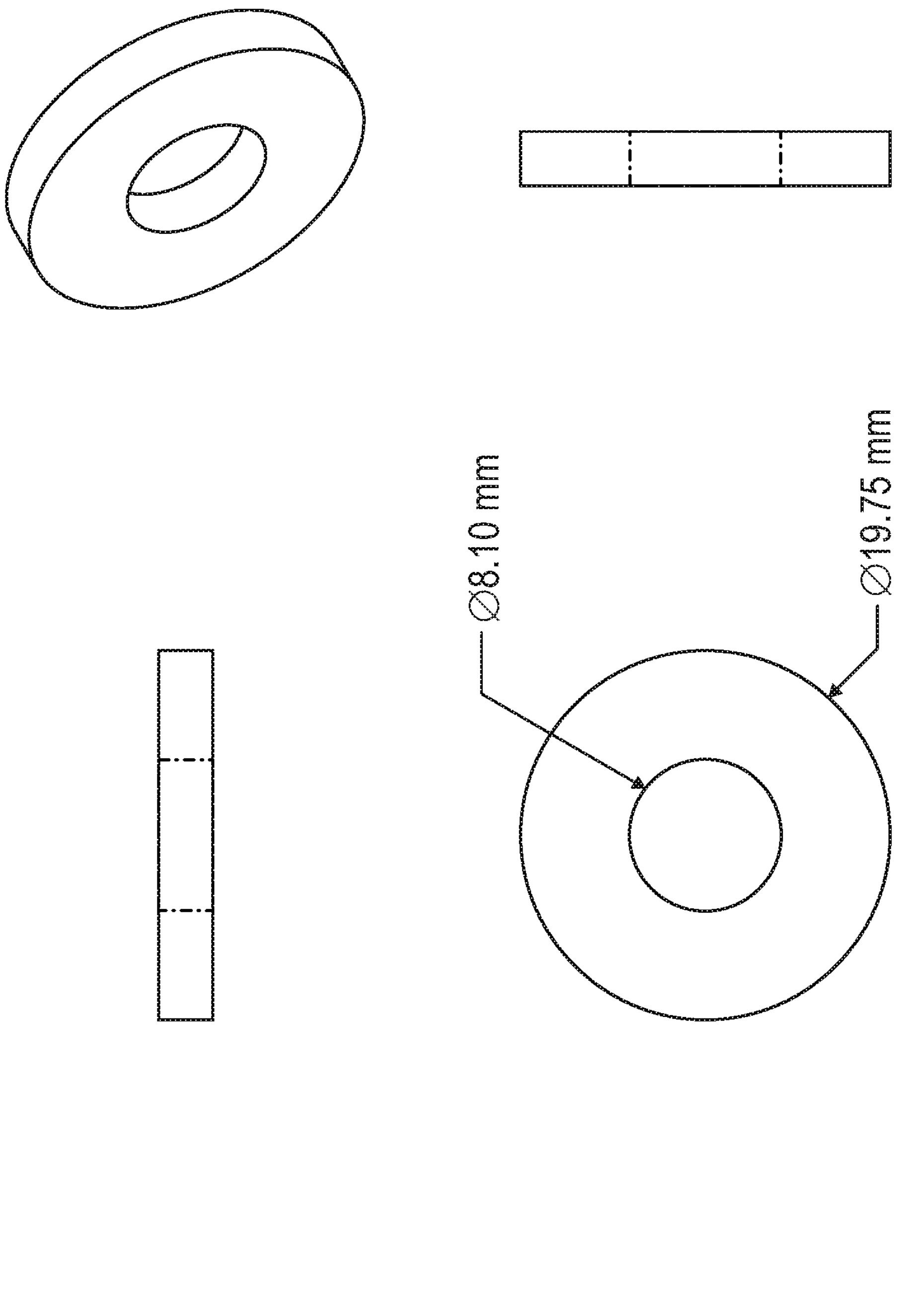
Figure 7C:
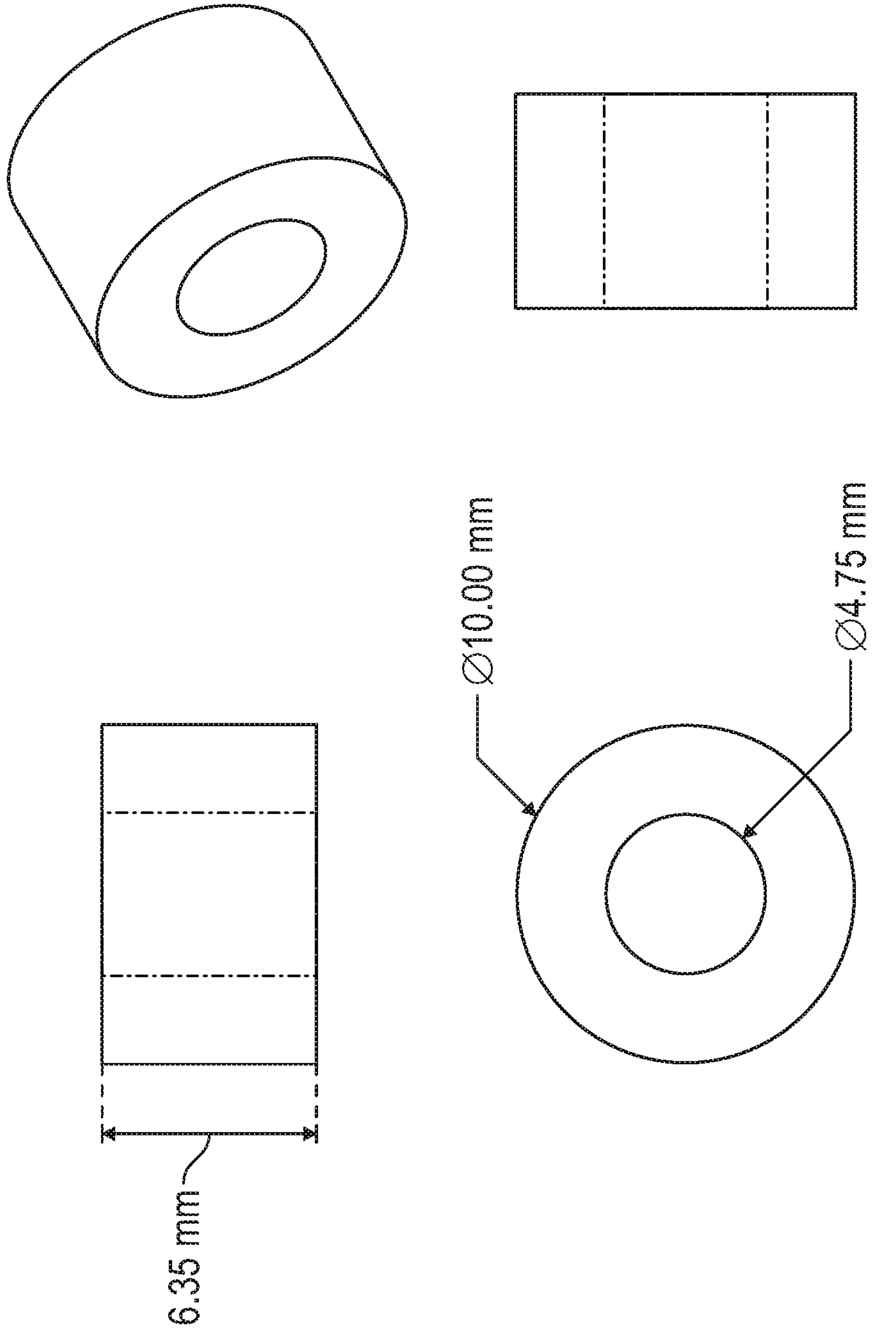
FIG. 7C is an illustration of the gasket for the plunger, in accordance with embodiments of the present disclosure.

Rubber Rings for Stylet and Plunger:

In an embodiment, to ensure that the stylet base and plunger funnel can fit inside the device, the diameters are 2.5 mm smaller than the respective diameters of the holes into which they fit. This creates a small gap in the device which could cause contamination. To seal the device from the environment, rubber rings were designed to fit onto the stylet base (FIG. 7A corresponding to stylet in FIG. 5A, FIG. 7B corresponding to plungers in FIGS. 4A and 4B, and FIG. 7C corresponding to plungers in FIGS. 4C and 4D). The embodiment in FIG. 7A spans the distance of the 1.25 mm gap on each side. The rubber ring for the stylet has an outer diameter of 4 mm, inner diameter of 3 mm, and a height of 4 mm. In some embodiments, the rubber ring for the plunger has an outer diameter of 20 mm, inner diameter of 9.5 mm, and a height of 3 mm.

In some embodiments (such as shown in FIGS. 4C and 4D, the plunger geometry features a shelf where the radius of the cylindrical channel that the stylet is guided through is reduced to prevent the stylet from advancing past the lesion site and can be used without t a rubber stopper.

Figure 5A:
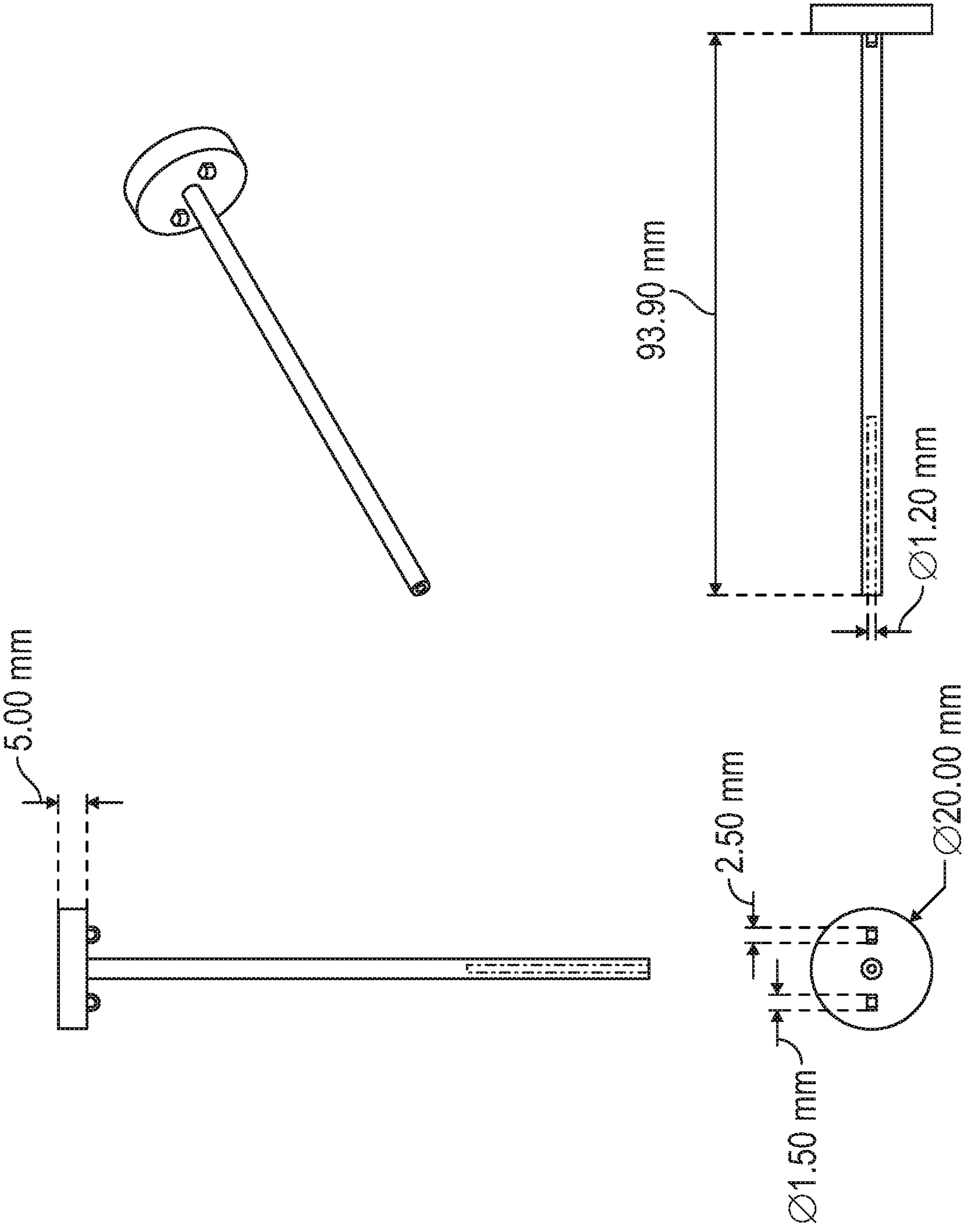
FIGS. 5A and 5B are dimensioned drawings of the stylet plunger base in accordance with two possible embodiments of the present disclosure.
Figure 5B:
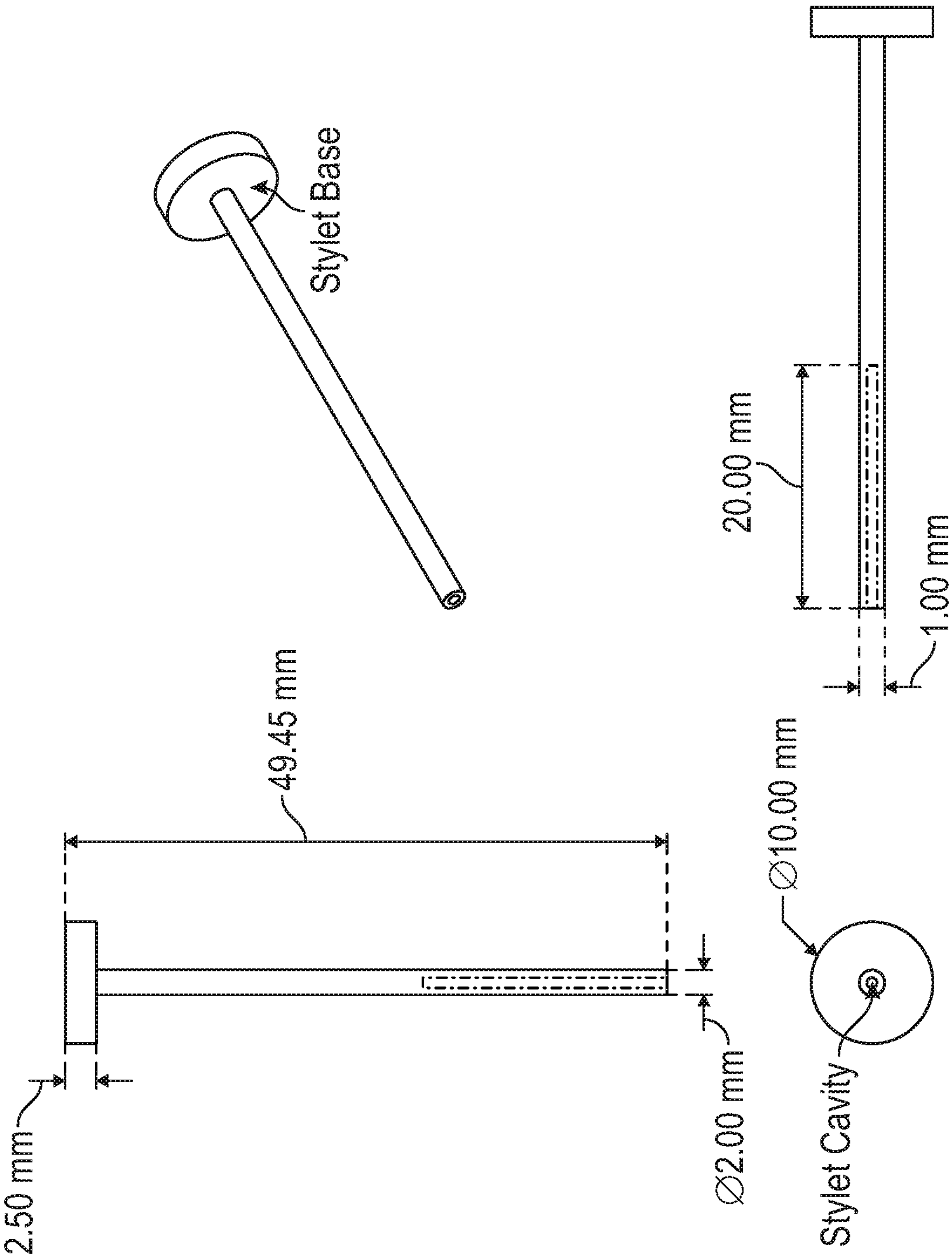

Spring and Loops for the Spring:

In some embodiments, on both the bottom side of the stylet base flange and the top side of the plunger flange there are loops used to hold a spring (visible in FIGS. 4A and 5A). The spring keeps the tip of the stylet at the same position as the tip of plunger by pulling the stylet base, and therefore stylet, down with the plunger as it is moved. When not in use, the spring also acts as a safeguard to return the stylet to its rightful position if the stylet base were to be moved slightly. If the stylet tip is too far out of the plunger, it will push the tissue out of the pre-injection chamber when the plunger is pushed down to expel the liquid medium. If the stylet tip is too far inside of the plunger, fluid and the tissue may enter the empty space. Lastly, the spring offers a small amount of resistance proportional to its spring constant to help users control the speed of injection and deter them from pushing too quickly which could damage the neo-tissue.

In an embodiment, the spring's free length is about 3.2 inches and can compress at least 2.5 inches. So that the spring is not too stiff and that it is possible for users to easily use the device, the maximum spring constant should be no more than about 2 lbs/inch, which means it would require 5 lbs of force to compress the spring and inject the tissue. Other spring constants can be used for comfort of the user and device functionality as can be envisioned by one of ordinary skill in the art.

With a spring, users can easily control the speed at which the injection occurs, however the spring does not prevent them from pushing too fast or allow them to regulate the injection process. Alternatively, using a dashpot or hydraulic piston to control the movement of the stylet base and stylet instead of a spring, the same or a similar process can be predicted each time the neo-tissue injection device is used, and a velocity limit is imposed on the movement of the stylet base to ensure that the tissue will not be damaged due to excessive shear stresses and speed. The device can be provided with a spring, dashpot, or hydraulic piston depending on the needs of the user.

Device Variations:

As described above, the device can be modified. Several possible, but not exhaustive variations are presented herein. For example, in one embodiment (called D1), the fluid exchange chamber can have diamond-shaped holes and a conical shape. This embodiment can be seen in FIGS. 2A-2C and assembled in FIGS. 1A and 1B. Embodiment D1 can be used with the shell shown in FIG. 3A, the plunger in FIG. 4A or 4B, the stylet plunger in FIG. 5A, and the rubber stoppers in FIGS. 7A and 7B.

In another embodiment (called D2), the fluid exchange chamber can have circular holes and a conical shape. This embodiment can be seen in FIGS. 2D-2E and assembled in FIGS. 1C-1F. Embodiment D2 can be used with the shells shown in FIG. 3B-3C, the plunger in FIG. 4C, the stylet plunger in FIG. 5B, and the rubber stopper in FIG. 7C (the plunger in 4C does not use a rubber stopper).

In another embodiment (called D3), the fluid exchange chamber can have circular holes and a cylindrical chamber exiting into a funnel. This embodiment can be seen in FIG. 2F. Embodiment D3 can be used with the shells shown in FIG. 3B-3C, the plunger in FIG. 4D, the stylet plunger in FIG. 5B, and the rubber stopper in FIG. 7C (the plunger in 4D does not use a rubber stopper).

Storage and Transportation:

Advantageously, the neo-tissue injection device is able to store the neo-tissue within it for several days prior to injection (e.g., about 3 days at room temperature). The storage time is dependent upon tissue type, medium, and storage conditions. After the neo-tissue and liquid growth medium have been loaded into the device, a Luer lock cap will block the end where a needle will be later attached and the plunger and stylet will block the opposite end. The cap and rubber pieces around the plunger and stylet base create airtight seals to maintain sterility within the capsule and prevent leakage of any fluid. To ensure that the assembly stays together, the rubber pieces provide enough friction to counteract small disruptions that can accumulate and lead to separation over time. The spring will also keep the stylet base and plunger connected together and in the same position with respect to one another.

For packaging during transportation, bags similar to those used for storage of syringes or to autoclave bags can be used. A 3D printed container that completely encapsulates the device can also be produced, which can keep the parts together better by protecting the device from forces and perturbations during storage and transportation.

Sterility:

Even if sterility is not maintained on the outside surfaces of the device, the inside of the capsule and the fluid-exchange chamber where the neo-tissue and liquid growth medium is sealed from the outside world, and thus remains sterile and prevents contamination.

Ideally, the neo-tissue injection device would be manufactured and packaged sterilely, but for purposes of the prototype and extra considerations of other potential sterilization processes, use of ethylene oxide gas, autoclaving, and more general washing processes were investigated. Although it is the most common sterilization process, autoclaving should not be used when parts have been made from 3D printed plastic resin which will melt under the high temperatures used in autoclaving. Other washing processes, such as using chlorhexidine and ethanol may not be effective because of all the small holes and components that will be unreachable with wipes and sponges. Sterilization with ethylene oxide gas which occurs in lower temperature is an option to effectively clean the device while preventing damage to the parts. The device is sterilized before loading with the tissue. The tissue, which has been grown in a sterile environment is loaded into the device under sterile conditions.

Figure 8:
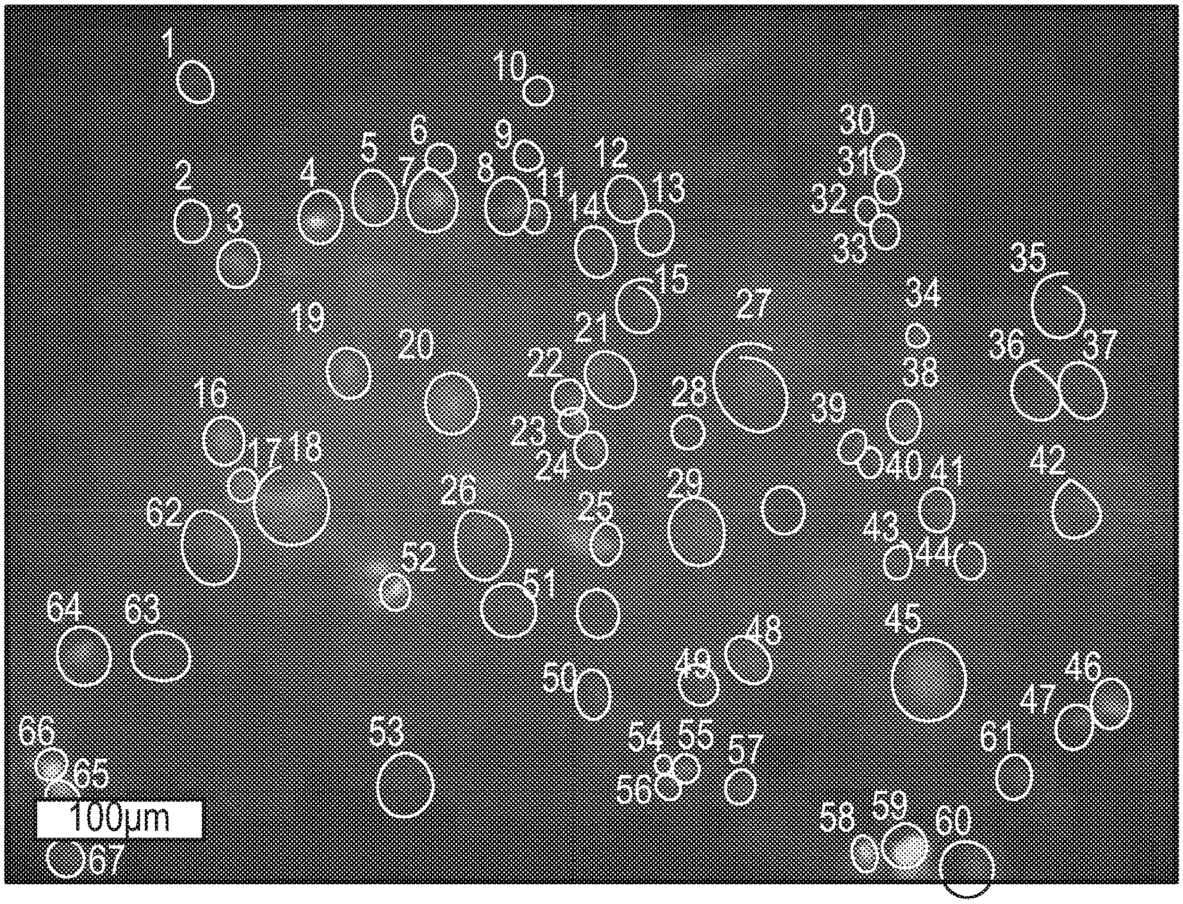
FIG. 8 shows an example of a cell count image in pre-injection stromal medium.

Cell Viability Analysis:

Cell viability tests were conducted using a functional prototype of the device. The cells were injected into a cadaver horse specimen containing the suspensory ligament and superficial digital flexion tendon, where the injection site was the superficial digital flexor tendon. The data set contained 4 groups: 1) Cells in stromal medium before injection; 2) Cells in stromal medium after injection; 3) Cells in tenogenic medium before injection; and 4) Cells in tenogenic medium after injection. There were n=5 samples for each group (5 images per group with a total of 20 images). The cells in each of the images were counted, and each group member (members A-E in Table 1) counted the cells for one image of a given group to decrease the effects of observer error. FIG. 8 shows an example of a cell count image in pre-injection stromal medium.

Figure 9A:
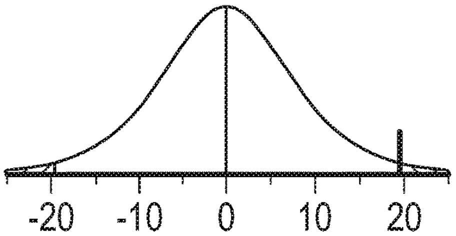
FIGS. 9A and 9B show cell viability data for stromal and tenogenic media, respectively).
Figure 9B:
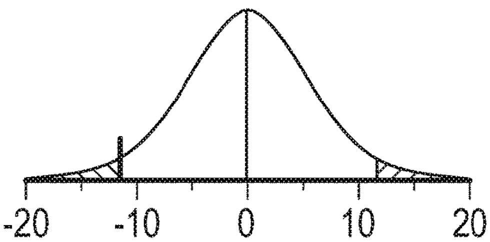
Figure 9C:
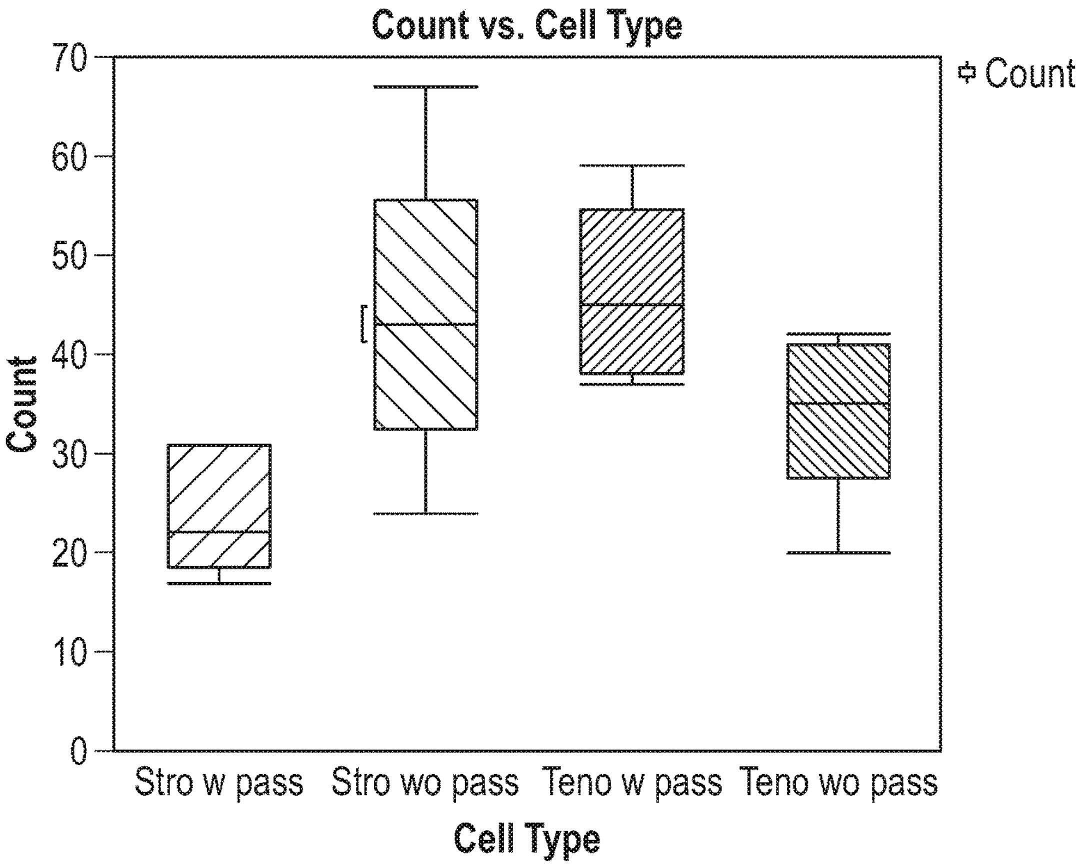
FIG. 9C is a boxplot showing the variance between the groups.

A one-tailed t-test was conducted between the cells of the same medium before and after injection. Cells in stromal medium were compared pre- and post-injection, and the cells in tenogenic medium were compared pre- and post-injection. A one-tailed test was chosen because it was expected that more cells will be alive before injection than after injection due to the forces during the injection process that can cause cell death. An alpha value of 0.05 indicates significance. The statistical tests were conducted in JMP, and the output of the tests is shown below in Table 2 and FIGS. 9A-B (stromal and tenogenic media, respectively). A box-plot was also created to depict the variance between the groups (FIG. 9C).

TABLE 1

| | Stro wo pass | Stro w pass | Teno wo pass | Teno w pass |
|---|---|---|---|---|
| A | 24 | 31 | 35 | 39 |
| B | 44 | 20 | 35 | 45 |
| C | 43 | 31 | 42 | 50 |
| D | 67 | 17 | 20 | 59 |
| E | 41 | 22 | 40 | 37 |
| Average | 43.8 | 24.2 | 34.4 | 46 |

Figure 10A:
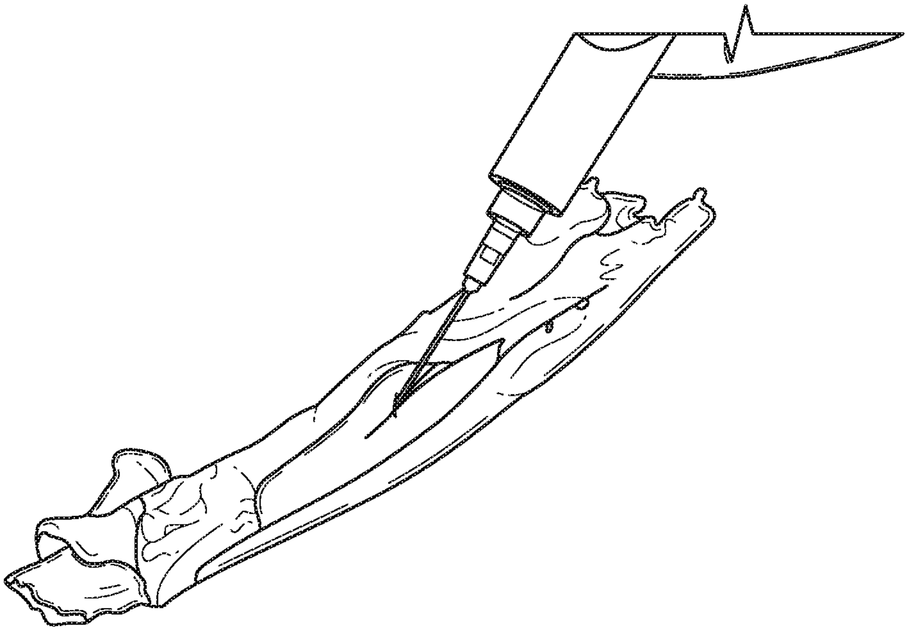
FIGS. 10A and 10B are camera images of injection of collagen into an equine tendon using the device, and the successful injection site (circled), respectively.
Figure 10B:
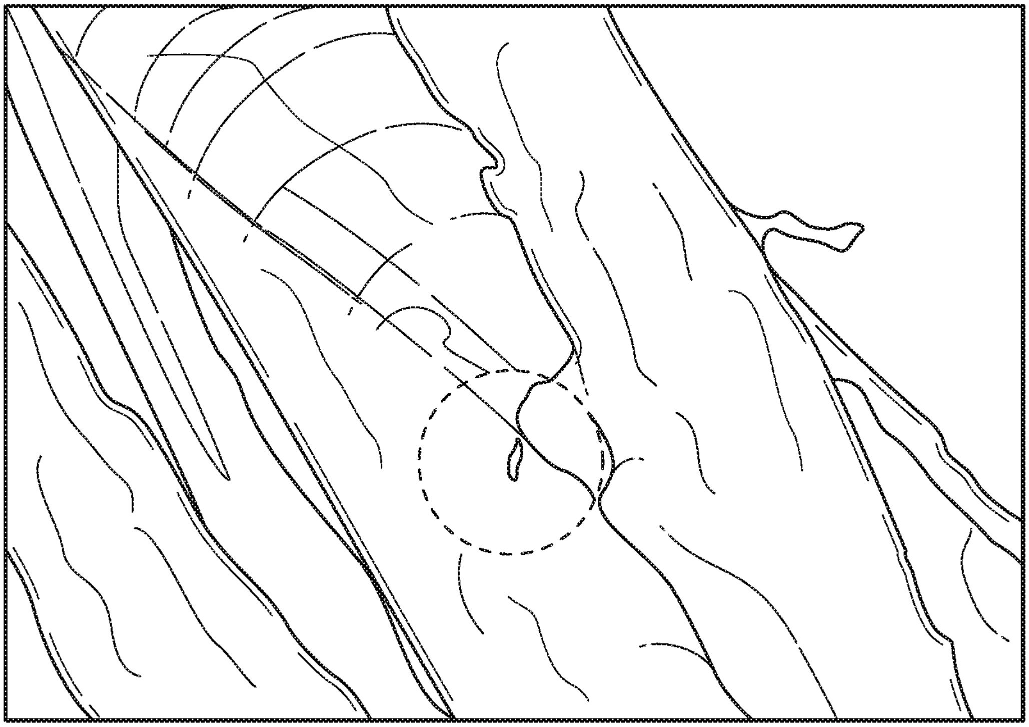

FIGS. 10A and 10B are camera images of injection of collagen into an equine tendon using the device, and the successful injection site (circled), respectively.

The cells remain viable when injected through the device. Based on recent studies (not shown), tendon neotissue integrates into existing tissue and remains viable for about 6 weeks after injection.

REFERENCES

Amer, M. H., Rose, F., Shakesheff, K. M., & White, L. J. (2018). A biomaterials approach to influence stem cell fate in injectable cell-based therapies. Stem cell research & therapy, 9(1), 39. https://doi.org/10.1186/s13287-018-0789-1

Andarawis-Puri, N., Flatow, E. L., & Soslowsky, L. J. (2015). Tendon basic science: Development, repair, regeneration, and healing. Journal of orthopaedic research: official publication of the Orthopaedic Research Society, 33(6), 780-784. https://doi.org/10.1002/jor.22869

Bertuglia, A., Bullone, M., Rossotto, F. et al. Epidemiology of musculoskeletal injuries in a population of harness Standardbred racehorses in training. BMC Vet Res 10, 11 (2014). https://doi.org/10.1186/1746-6148-10-11

Kim, Y. S., Sung, C. H., Chung, S. H., Kwak, S. J., & Koh, Y. G. (2017). Does an Injection of Adipose-Derived Mesenchymal Stem Cells Loaded in Fibrin Glue Influence Rotator Cuff Repair Outcomes? A Clinical and Magnetic Resonance Imaging Study. The American journal of sports medicine, 45(9), 2010-2018. https://doi.org/10.1177/0363546517702863

Paredes, J. J., & Andarawis-Puri, N. (2016). Therapeutics for tendon regeneration: a multidisciplinary review of tendon research for improved healing. Annals of the New York Academy of Sciences, 1383(1), 125-138. https://doi.org/10.1111/nyas.13228

Wang, Y., Jin, S., Luo, D., He, D., Shi, C., Zhu, L., . . . Liu, Y. (2021). Functional regeneration and repair of tendons using biomimetic scaffolds loaded with recombinant periostin. Nature Communications, 12(1), 1293. doi: 10.1038/s41467-021-21545-1

Yang, G., Rothrauff, B. B., & Tuan, R. S. (2013). Tendon and ligament regeneration and repair: clinical relevance and developmental paradigm. Birth defects research. Part C, Embryo today: reviews, 99(3), 203-222. https://doi.org/10.1002/bdrc.21041

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that measurements, amounts, and other numerical data can be expressed herein in a range format. It is also understood that there are a number of values disclosed herein, and that each value is also herein disclosed as "approximately" that particular value in addition to the value itself. For example, if the value "10" is disclosed, then "approximately 10" is also disclosed. Similarly, when values are expressed as approximations, by use of the antecedent "approximately," it will be understood that the particular value forms a further aspect. For example, if the value "approximately 10" is disclosed, then "10" is also disclosed.

As used herein, the terms "about," "approximately," "at or about," and "substantially equal" can mean that the amount or value in question can be the exact value or a value that provides equivalent results or effects as recited in the claims or taught herein. That is, it is understood that amounts, sizes, measurements, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In general, an amount, size, measurement, parameter or other quantity or characteristic is "about," "approximate," "at or about," or "substantially equal" whether or not expressly stated to be such. It is understood that where "about," "approximately," "at or about," or "substantially equal" is used before a quantitative value, the parameter also includes the specific quantitative value itself, unless specifically stated otherwise.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

What is claimed is:

1. An injection device for delivery of viable neotissue comprising:

a fluid exchange chamber having a funneled portion, the funneled portion having a bottom connected to a pre-injection tube, wherein the fluid exchange chamber comprises fluid transfer holes extending through an outer surface of the fluid exchange chamber;

a cylindrical outer shell comprising a central bore connecting a top inlet and a bottom outlet, wherein the fluid exchange chamber is disposed in the outer shell and wherein the pre-injection tube exits the shell via the bottom outlet;

a first plunger having a central channel and a tapered bottom, wherein the tapered bottom mates with an inside of the funneled portion when depressed; and a stylet plunger disposed in the central channel, wherein the fluid exchange chamber comprises a threaded base surrounding the pre-injection tube and a complementary threaded ring inside a bottom of the outer shell such that the fluid exchange chamber is threadably coupled to an interior surface of the outer shell.

2. The device according to claim 1, further comprising a male Luer lock needle fitting in the threaded base.

3. The device according to claim 1, wherein the shell comprises a male Luer lock needle fitting in an outer bore.

4. The device according to claim 1, wherein the first plunger comprises a flexible seal that prevents fluid from escaping the top inlet.

5. The device according to claim 1, wherein the first plunger comprises a flange at a top end.

6. The device according to claim 1, wherein the stylet plunger comprises a base having a flange and a stylet cavity, and wherein a stylet is disposed in the stylet cavity.

7. The device according to claim 1, wherein the stylet plunger further comprises a flexible seal that prevents fluid from escaping the central channel of the first plunger.

8. The device according to claim 1, further comprising a removable cap coupled to a Luer lock needle fitting when a needle is not attached to the device.

9. The device according to claim 1, wherein the central bore of the outer shell comprises a bottom cavity dimensioned to house the fluid exchange chamber, a middle cavity dimensioned to receive the tapered bottom of the first plunger when depressed, and a top cavity dimensioned to receive a top portion of the first plunger.

10. An injection device for delivery of viable neotissue comprising:

a fluid exchange chamber having a funneled portion, the funneled portion having a bottom connected to a pre-injection tube, wherein the fluid exchange chamber comprises fluid transfer holes extending through an outer surface of the fluid exchange chamber;

a cylindrical outer shell comprising a central bore connecting a top inlet and a bottom outlet, wherein the fluid exchange chamber is disposed in the outer shell and wherein the pre-injection tube exits the shell via the bottom outlet;

a first plunger having a central channel and a tapered bottom, wherein the tapered bottom mates with an inside of the funneled portion when depressed; and a stylet plunger disposed in the central channel, wherein the fluid transfer holes are angled upward from an inner surface of the fluid exchange chamber to the outer surface of the fluid exchange chamber.

11. The device according to claim 10, wherein the fluid exchange chamber comprises a threaded base surrounding the pre-injection tube and a complementary threaded ring inside a bottom of the outer shell such that the fluid exchange chamber is threadably coupled to an interior surface of the outer shell.

12. An injection device for delivery of viable neotissue comprising:

a fluid exchange chamber having a funneled portion, the funneled portion having a bottom connected to a pre-injection tube, wherein the fluid exchange chamber comprises fluid transfer holes extending through an outer surface of the fluid exchange chamber;

a cylindrical outer shell comprising a central bore connecting a top inlet and a bottom outlet, wherein the fluid exchange chamber is disposed in the outer shell and wherein the pre-injection tube exits the shell via the bottom outlet;

a first plunger having a central channel and a tapered bottom, wherein the tapered bottom mates with an inside of the funneled portion when depressed; and a stylet plunger disposed in the central channel, wherein the fluid transfer holes have a smaller diameter on an inner surface of the fluid exchange chamber than on the outer surface.

13. An injection device for delivery of viable neotissue comprising:

a fluid exchange chamber having a funneled portion, the funneled portion having a bottom connected to a pre-injection tube, wherein the fluid exchange chamber comprises fluid transfer holes extending through an outer surface of the fluid exchange chamber;

a cylindrical outer shell comprising a central bore connecting a top inlet and a bottom outlet, wherein the fluid exchange chamber is disposed in the outer shell and wherein the pre-injection tube exits the shell via the bottom outlet;

a first plunger having a central channel and a tapered bottom, wherein the tapered bottom mates with an inside of the funneled portion when depressed; and a stylet plunger disposed in the central channel wherein a stylet base flange and a plunger flange are connected by a spring or a piston.

14. An injection device for delivery of viable neotissue comprising:

a fluid exchange chamber having a funneled portion, the funneled portion having a bottom connected to a pre-injection tube, wherein the fluid exchange chamber comprises:

fluid transfer holes extending through an outer surface of the fluid exchange chamber, wherein the fluid transfer holes are angled upward from an inner surface of the fluid exchange chamber to the outer surface of the fluid exchange chamber and wherein the fluid transfer holes have a smaller diameter on the inner surface of the fluid exchange chamber than on the outer surface, and a threaded base surrounding the pre-injection tube and a complementary threaded ring inside a bottom of a cylindrical outer shell such that the fluid exchange chamber is threadably coupled to an interior surface of the outer shell;

the outer shell comprising a central bore connecting a top inlet and a bottom outlet, wherein the fluid exchange chamber is disposed in the outer shell and wherein the pre-injection tube exits the shell into the bottom outlet;

a first plunger having a central channel and a tapered bottom, wherein the tapered bottom mates with an inside of the funneled portion when depressed;

a male Luer lock needle fitting in the threaded base; and a stylet plunger disposed in the central channel, wherein the stylet plunger comprises a base having a flange and a stylet cavity, and wherein a stylet is disposed in the stylet cavity.

* * * * *